US012742755B2

(12) United States Patent
Xu et al.

(10) Patent No.: US 12,742,755 B2
(45) Date of Patent: Sep. 22, 2026

(54) METHODS FOR IDENTIFYING SULFUR-TREATED FOOD PRODUCTS

(71) Applicant: Hong Kong Baptist University, Hong Kong (CN)

(72) Inventors: Jun Xu, Hong Kong (CN); Weihao Zhang, Hong Kong (CN); Kam Chun Chan, Hong Kong (CN); Yui Man Chan, Hong Kong (CN); Hanyan Luo, Hong Kong (CN)

(73) Assignee: Hong Kong Baptist University, Hong Kong (CN)

( * ) Notice: Subject to any disclaimer, the term of this patent is extended or adjusted under 35 U.S.C. 154(b) by 291 days.

(21) Appl. No.: 18/635,099

(22) Filed: Apr. 15, 2024

(65) Prior Publication Data

US 2025/0093311 A1 Mar. 20, 2025

Related U.S. Application Data

(60) Provisional application No. 63/583,943, filed on Sep. 20, 2023.

(51) Int. Cl.

| | |
|---|---|
| ***G01N 33/02*** | (2006.01) |
| ***B01D 15/16*** | (2006.01) |
| ***G01N 30/72*** | (2006.01) |
| ***G01N 30/88*** | (2006.01) |
| ***H01J 49/00*** | (2006.01) |
| *G01N 30/02* | (2006.01) |

(52) U.S. Cl.

CPC ....... *G01N 30/7233* (2013.01); *B01D 15/163* (2013.01); *G01N 30/88* (2013.01); *G01N 33/02* (2013.01); *H01J 49/004* (2013.01); *G01N 2030/027* (2013.01); *G01N 2030/884* (2013.01)

(58) Field of Classification Search

CPC ........ G01N 33/00; G01N 33/02; G01N 30/72; G01N 30/7233; G01N 30/88; G01N 2030/027; G01N 2030/884; B01D 15/16; B01D 15/163

See application file for complete search history.

(56) References Cited

U.S. PATENT DOCUMENTS

2024/0310348 A1 * 9/2024 Granevitze ............ B65D 79/02

FOREIGN PATENT DOCUMENTS

| | | | | |
|---|---|---|---|---|
| CN | 105403550 A | * | 3/2016 | ............. G01N 21/31 |
| CN | 107144652 A | * | 9/2017 | ............. G01N 30/02 |
| CN | 107957417 A | * | 4/2018 | ............. G01N 21/78 |
| CN | 110865142 A | * | 3/2020 | ............. G01N 30/06 |
| CN | 114062558 A | * | 2/2022 | ............. G01N 30/02 |

(Continued)

OTHER PUBLICATIONS

Machine Translation of CN-107144652-A (Year: 2017).*

(Continued)

*Primary Examiner* — Nguyen Q. Ha

(74) *Attorney, Agent, or Firm* — S&F/WEHRW

(57) ABSTRACT

A method of identifying a sulfur-treated food product, the method including: providing a sample including a food product; analyzing the sample using an analytical method to determine whether the sample includes tryptophan sulfonate; and identifying based on whether the sample includes tryptophan sulfonate that the food product is sulfur-treated, wherein the presence of tryptophan sulfonate indicates that the food product is sulfur-treated.

20 Claims, 35 Drawing Sheets

(56) References Cited

FOREIGN PATENT DOCUMENTS

| | | | | |
|---|---|---|---|---|
| CN | 114216979 B | * 8/2023 | ............ | G01N 30/02 |
| WO | WO-2016107516 A1 | * 7/2016 | ............ | G01N 21/65 |

OTHER PUBLICATIONS

Machine Translation of CN-114216979-B (Year: 2023).*
Machine Translation of CN-105403550-A (Year: 2015).*
Machine Translation of CN-107957417-A (Year: 2018).*
Machine Translation of CN-110865142-A (Year: 2020).*
Machine Translation of CN-114062558-A (Year: 2022).*
Machine Translation of WO-2016107516-A1 (Year: 2016).*
Carlos, K. S.; Conrad, S. M.; Handy, S. M.; de Jager, L. S. (2020). Investigation of food products containing garlic or onion for a false positive sulphite response by LC-MS/MS. Food Addit Contam—Part A Chem Anal Control Expo Risk Assess, 37(5), 723-730. DOI: 10.1080/19440049.2020.1727965.
Carlos, K. S.; de Jager, L. S. (2017). Determination of Sulfite in Food by Liquid Chromatography Tandem Mass Spectrometry: Collaborative Study. J AOAC Int, 100(6), 1785-1794. DOI: 10.5740/jaoacint.17-0033. DOI: 10.5740/jaoacint.17-0033.
Chan, Y. M.; Lu, B. W.; Zhang, W. H.; Chan, K. C.; Fang, J.; Luo, H. Y.; Du, J.; Zhao, Z. Z.; Chen, H. B.; Xu, J. (2023). Impact of Sulfur Fumigation on the Chemistry of Dioscoreae Rhizoma (Chinese Yam). ACS omega, 8(23), 21293-21304. DOI: 10.1021/acsomega.3c02729.
Duan, S. M.; Xu, J.; Bai, Y. J.; Ding, Y.; Kong, M.; Liu, H. H.; Li, X. Y.; Zhang, Q. S; Chen, H. B.; Liu, L. F.; Li, S. L. (2016). Sulfur dioxide residue in sulfur-fumigated edible herbs: The fewer, the safer?. Food Chem, 192, 119-124. DOI: 10.1016/j.foodchem.2015.07.003.
Genualdi, S.; DeJager, L. (2021). Determination of Sulfites in Food using Liquid Chromatography-Tandem Mass Spectrometry (LC-MS/MS). U.S. Food and Drug Administration, 1-16.
Li, S. L.; Shen, H.; Zhu, L. Y.; Xu, J.; Jia, X. B.; Zhang, H. M.; Lin, G.; Cai, H.; Cai, B. C.; Chen, S. L.; Xu, H. X. (2012). Ultra-high-performance liquid chromatography-quadrupole/time of flight mass spectrometry based chemical profiling approach to rapidly reveal chemical transformation of sulfur-fumigated medicinal herbs, a case study on white ginseng. J Chromatogr A, 1231, 31-45. DOI: 10.1016/j.chroma.2012.01.083.
Robbins, K. S.; Shah, R.; MacMahon, S.; De Jager, L. S. (2015). Development of a liquid chromatography-tandem mass spectrometry method for the determination of sulfite in food. J Agric Food Chem, 63(21), 5126-5132. DOI: 10.1021/jf505525z.
Wu, C. Y.; Kong, M.; Zhang, W.; Long, F.; Zhou, J.; Zhou, S. S.; Xu, J. D.; Xu, J.; Li, S. L. (2018). Impact of sulphur fumigation on the chemistry of ginger. Food Chem, 239, 953-963. DOI: 10.1016/j.foodchem.2017.07.033.
Xu, F.; Kong, M.; Xu, J. D.; Xu, J.; Jiang, Y.; Li, S. L. (2020). Effects of sulfur fumigation and heating desulfurization on quality of medicinal herbs evaluated by metabolomics and glycomics: Codonopsis Radix, a pilot study. J Pharm Biomed Anal, 191, 113581. DOI: 10.1016/j.jpba.2020.113581.
Xu, Y. Y.; Long, F.; Zhang, Y. Q.; Xu, J. D.; Kong, M.; Li, S. L. (2018). Chemical markers for quality control of bran-fried sulfur-fumigated Paeoniae Radix Alba. J Pharm Biomed Anal, 159, 305-310. DOI: 10.1016/j.jpba.2018.07.003.

* cited by examiner

A
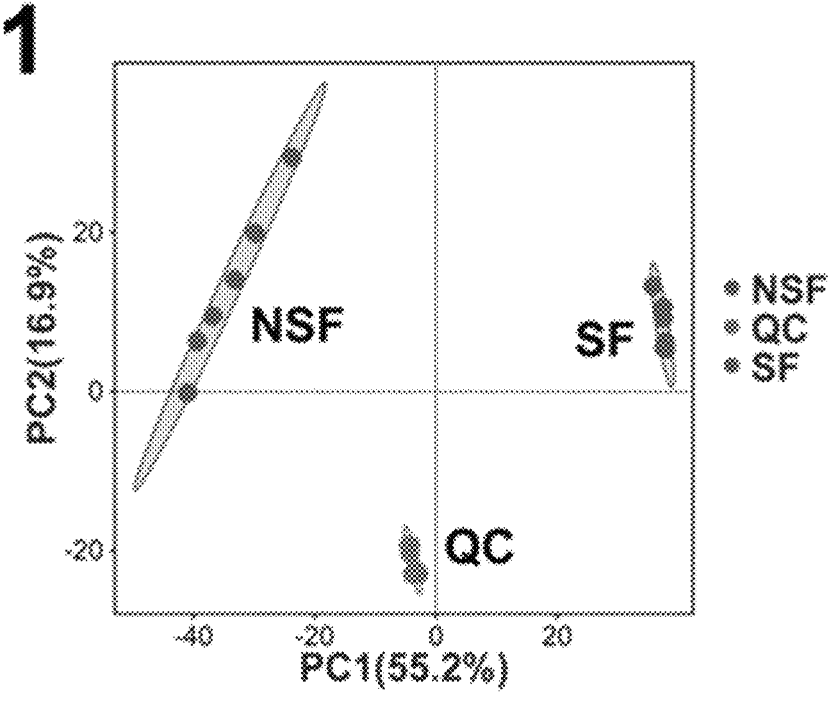
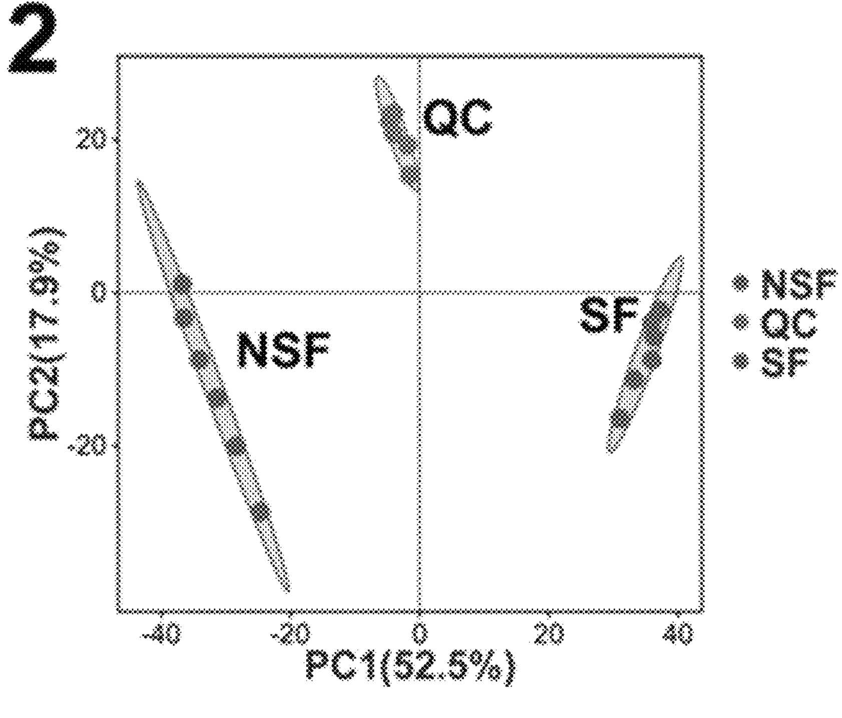
FIG. 1

B
1
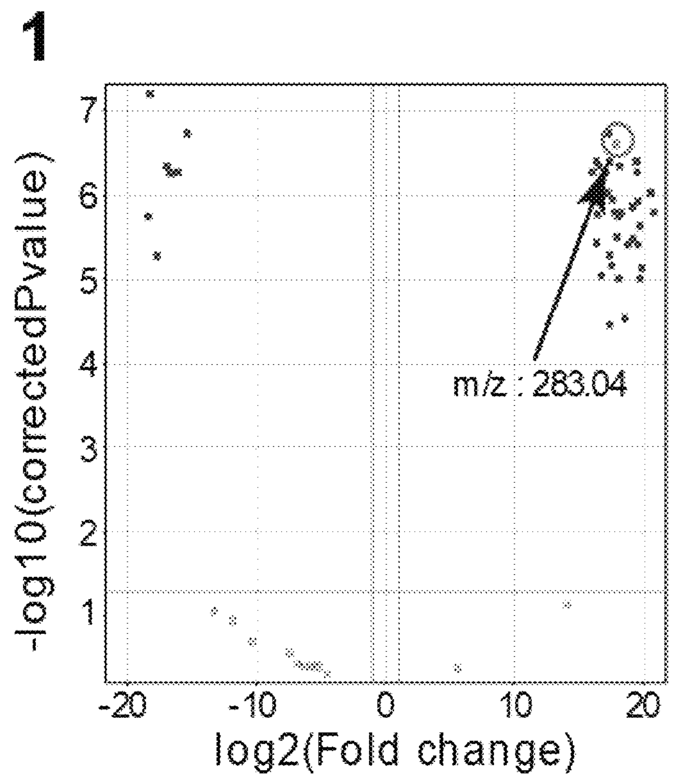
2
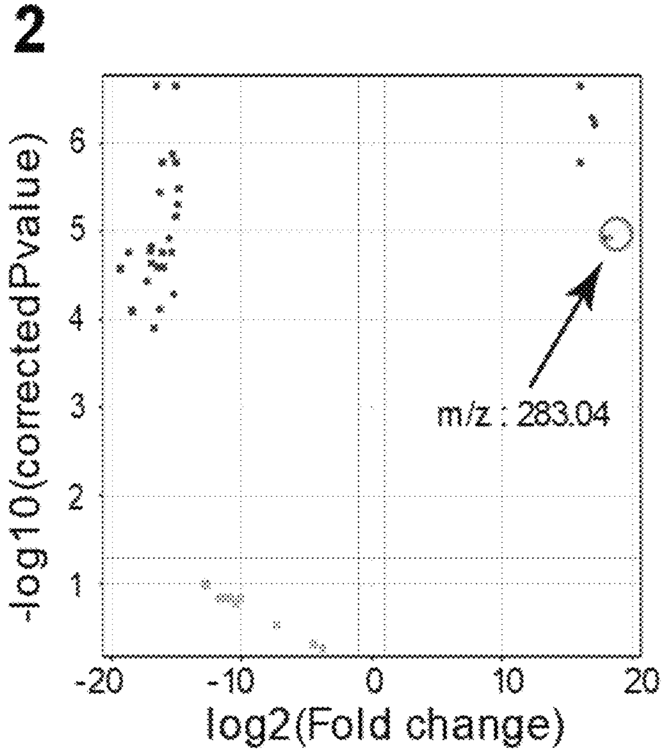
FIG. 1 (Continued)

C
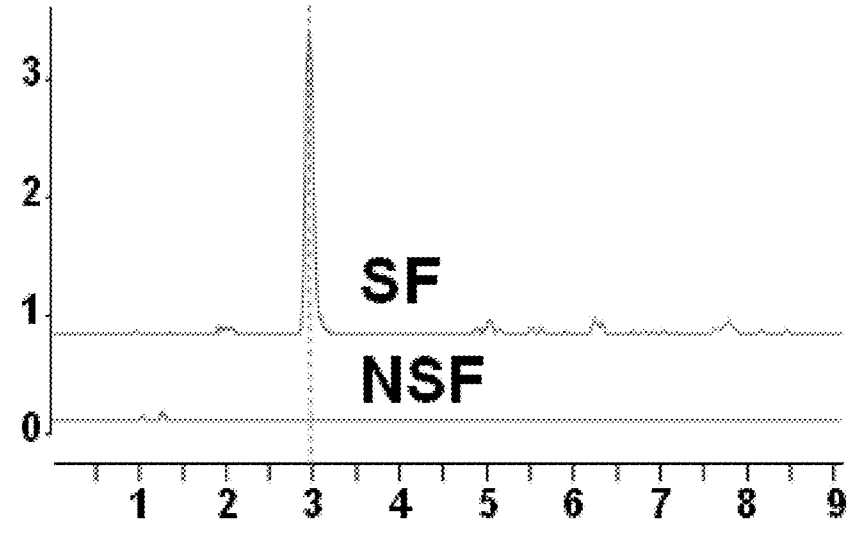
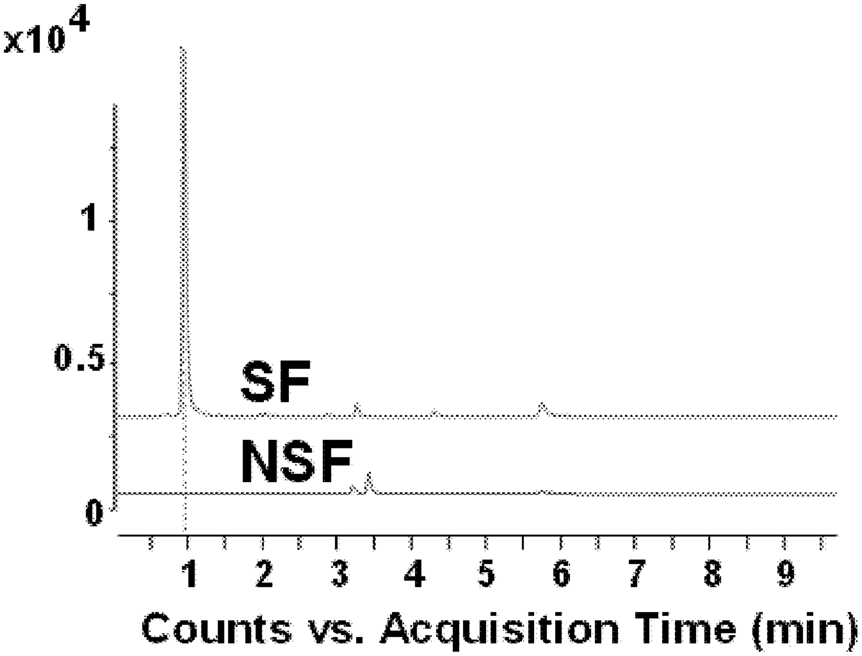
FIG. 1 (Continued)

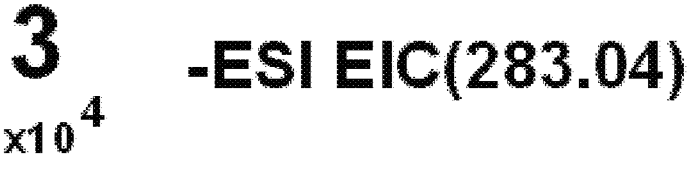
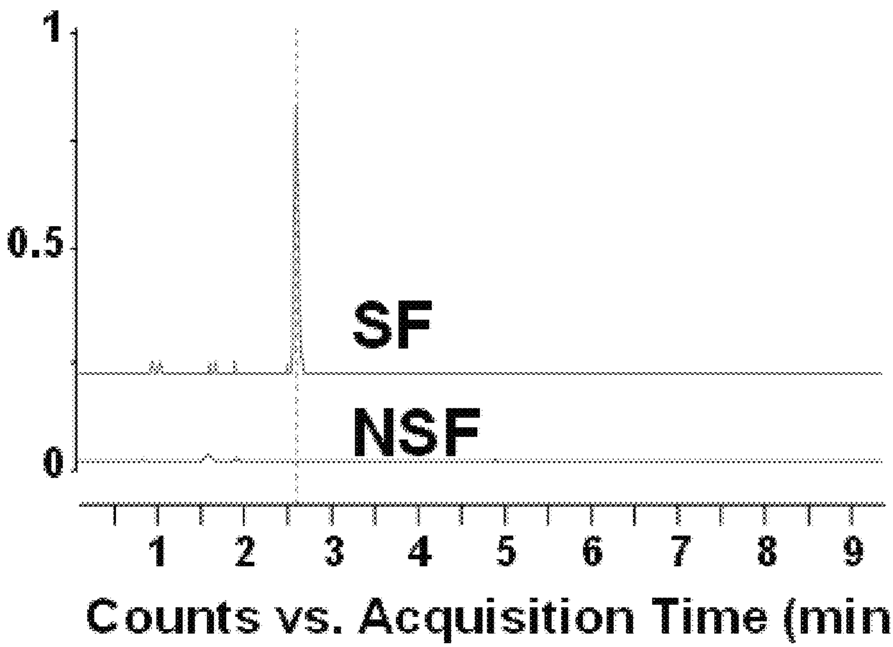
FIG. 1 (Continued)

A

B
Tryptophan
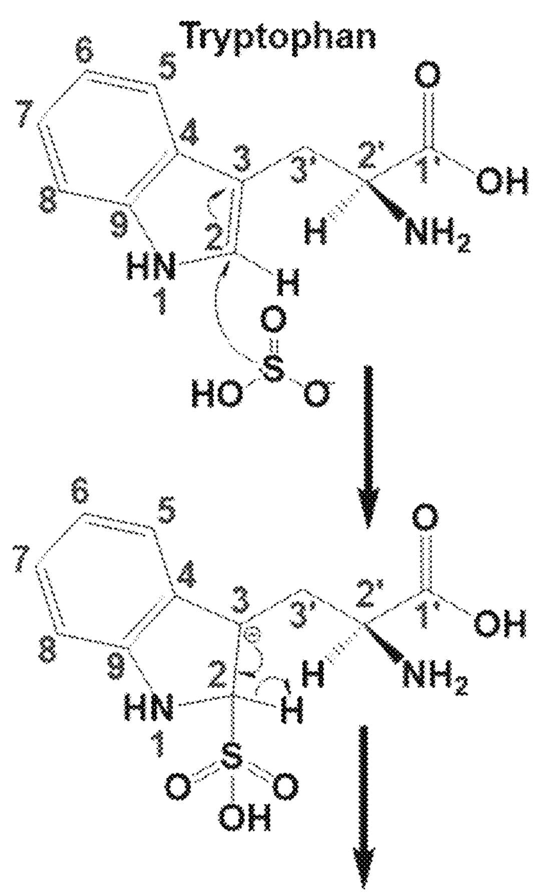
Tryptophan sulfonate
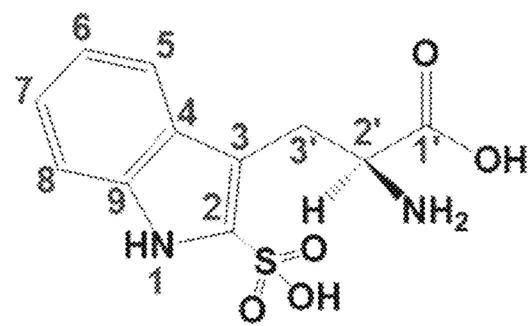
FIG. 2 (Continued)

A

| Sample | Tryptophan sulfonate content (mg/kg) |
|---|---|
| NSF Kiwi | 0 |
| NSF Guava | 0 |
| NSF Longan | 0 |
| NSF Peach | 0 |
| NSF Papaya | 0 |
| NSF Fig | 0 |
| NSF Banana | 0 |
| NSF Strawberry | 0 |
| NSF Grape | 0 |
| NSF Pineapple | 0 |
| NSF Blueberry | 0 |
| NSF Jujube | 0 |
| NSF Apricot | 0 |
| NSF Potato | 0 |
| NSF Garlic | 0 |
| NSF Onion | 0 |
| NSF Corn | 0 |
| NSF Mango | 0 |
| NSF Snow fungus | 0 |
| NSF Starfruit | 0 |
| SF Kiwi | 0.78±0.05 |
| SF Guava | 4.42±0.16 |
| SF Longan | 2.26±0.03 |
| SF Peach | 3.82±0.03 |
| SF Papaya | 3.76±0.07 |
| SF Fig | 8.49±0.06 |
| SF Banana | 1.9±0.04 |
| SF Strawberry | 5.62±0.06 |
| SF Grape | 2.67±0.08 |
| SF Pineapple | 10.7±0.27 |
| SF Blueberry | 0.55±0.01 |

All data are presented as Mean±SD.

FIG. 3

| | |
|---|---|
| SF Jujube | 0.25±0.02 |
| SF Apricot | 3.5±0.08 |
| SF Potato | 15.67±0.48 |
| SF Garlic | 13.35±0.05 |
| SF Onion | 8.1±0.17 |
| SF Corn | 4.64±0.1 |
| SF Mango | 5.79±0.13 |
| SF Snow fungus | 6.76±0.3 |
| SF Starfruit | 2.66±0.36 |

All data are presented as Mean±SD.

B

| | $SO_2$ content (mg/kg) | Tryptophan content (mg/kg) | Tryptophan sulfonate content (mg/kg) |
|---|---|---|---|
| ***Amomum kravanh* fruit** | 56.6±4.01 | 26.04±2.3 | 2.9±0.14 |
| ***Anemarrhena asphodeloides* rhizome** | 467.73±9.72 | 243.33±7.65 | 1.02±0.2 |
| ***Angelica dahurica* root** | 1072.41±11.68 | 30.48±1.41 | 126.52±1.91 |
| ***Angelica sinensis* root** | 819.42±8.2 | 92.65±4.03 | 96.83±3.3 |
| ***Atractylodes macrocephala* rhizome** | 203.74±3.55 | 27.81±1.76 | 93.62±2.88 |
| ***Bletilla striata* tuber** | 134.22±6.93 | 24.45±0.84 | 8.46±0.08 |
| ***Codonopsis pilosula* root** | 39.08±3.14 | 34.46±0.42 | 1.78±0.05 |
| ***Dioscorea opposita* rhizome** | 40.35±3.07 | 26.26±0.27 | 8.51±0.02 |
| **Dried apple** | 951.25±7.22 | 26.25±0.08 | 0.79±0.04 |
| **Dried apricots** | 216.05±12.1 | 25.26±0.76 | 0.89±0.03 |
| **Dried ginger** | 63.18±7.94 | 24.95±0.81 | 14.18±0.06 |
| **Dried guaua** | 214.9±2.06 | 24.41±0.15 | 0.48±0.03 |
| **Dried peach** | 16.88±0.08 | 29.28±0.36 | 0.61±0.01 |

FIG. 3 (Continued)

| | | | |
|---|---|---|---|
| **Dried pear** | 54.61±2.63 | 24.5±0.11 | 0.63±0.02 |
| **Dried pineapple** | 189.68±10.35 | 29.57±0.03 | 0.1±0.02 |
| **Dried potato** | 11.5±1.99 | 25.3±0.67 | 0.18±0 |
| **Dried strawberry** | 225.82±5.17 | 24.88±0.16 | 14.97±0.23 |
| ***Gastrodia elata* tuber** | 463.97±12.89 | 24.59±0.18 | 3.8±0.04 |
| ***Glehnia littoralis* root** | 47.52±4.78 | 28.76±0.31 | 168.12±0.2 |
| ***Glycyrrhiza uralensis* root** | 206.69±7.79 | 42.07±0.84 | 1.48±0.09 |
| ***Ligusticum chuanxiong* rhizome** | 547.7±6.35 | 38.92±0.73 | 37.9±0.68 |
| ***Lilium brownii* bulb** | 119.44±22.15 | 72.68±2.41 | 0.43±0.08 |
| ***Ophiopogon japonicusroot* tuber** | 1054.24±7.94 | 26.95±0.65 | 3.6±0.42 |
| ***Paeonia lactiflora* root** | 1242.37±10.98 | 24.43±0.19 | 2.4±0.09 |
| ***Panax ginseng* root** | 134.5±9.12 | 26.27±0.32 | 11.65±0.28 |
| ***Platycodon grandiflorum* root** | 360.4±12.16 | 63.11±0.06 | 53.61±0.95 |
| ***Pueraria lobata* root** | 280.25±3.93 | 26.72±0.16 | 11.77±0.08 |
| **Raisins** | 400.73±10.4 | 28.86±0.09 | 1.61±0.08 |
| **Dried papaya** | 15.52±1.72 | 0 | 0.25±0.02 |
| **Corn starch** | 0 | 24.51±0.13 | 0.25±0.01 |
| **Dried star fruit** | 0 | 24.41±0.08 | 0.29±0 |
| **Dried mango** | 0 | 25.66±0.07 | 0.76±0.03 |
| **Snow fungus** | 0 | 26.3±0.16 | 0.22±0.01 |
| **Garlic** | 32.43±6.48 | 91.25±0.33 | 0 |
| **Onion** | 16.27±3.25 | 174.57±0.67 | 0 |
| **Cashew** | 0 | 81.24±0.89 | 0 |
| ***Citrus medica* fruit** | 0 | 31.24±0.41 | 0 |
| ***Crataegus pinnatifida* fruit** | 0 | 25.27±0.08 | 0 |
| **Dired banana** | 0 | 25.8±0.04 | 0 |
| **Dried blueberry** | 0 | 24.41±0.07 | 0 |
| **Dried figs** | 0 | 24.51±0.01 | 0 |
| **Dried kiwi** | 0 | 24.43±0.05 | 0 |
| **Dried longan pulp** | 0 | 47.11±0.11 | 0 |
| **Dired olives** | 0 | 26.71±0.11 | 0 |
| ***Lycium barbarum* fruit** | 0 | 84.05±2.18 | 0 |
| **Macadamia nut** | 0 | 33.72±0.22 | 0 |
| **Pistachios** | 0 | 36.36±0.18 | 0 |
| ***Prunus armeniaca* seed** | 0 | 46.38±0.37 | 0 |
| ***Pseudostellaria heterophylla* root** | 0 | 32.38±0.07 | 0 |
| ***Ziziphus jujuba* fruit** | 0 | 27.14±0.15 | 0 |

All data are presented as Mean±SD.

| Name | Collection location | Collection time |
|---|---|---|
| *Amomum kravanh* fruit | Hong Kong, China | 22/7/2022 |
| *Anemarrhena asphodeloides* rhizome | Hong Kong, China | 20/7/2022 |
| *Angelica dahurica* root | Hong Kong, China | 22/7/2022 |
| *Angelica sinensis* root | Hong Kong, China | 22/7/2022 |
| *Atractylodes macrocephala* rhizome | Hong Kong, China | 22/7/2022 |
| *Bletilla striata* tuber | Hong Kong, China | 5/8/2022 |
| *Codonopsis pilosula* root | Hong Kong, China | 5/8/2022 |
| *Dioscorea opposita* rhizome | Zhejiang, China | 22/7/2022 |
| Dried apple | Hong Kong, China | 10/8/2022 |
| Dried apricots | Hong Kong, China | 9/8/2022 |
| Dried ginger | Hunan, China | 9/8/2022 |
| Dried guaua | Hong Kong, China | 9/8/2022 |
| Dried peach | Hong Kong, China | 9/8/2022 |
| Dried pear | Hong Kong, China | 9/8/2022 |
| Dried pineapple | Hong Kong, China | 9/8/2022 |
| Dried potato | Hong Kong, China | 9/8/2022 |
| Dried strawberry | Hong Kong, China | 9/8/2022 |
| *Gastrodia elata* tuber | Hong Kong, China | 20/7/2022 |
| *Glehnia littoralis* root | Hong Kong, China | 22/7/2022 |
| *Glycyrrhiza uralensis* root | Hong Kong, China | 20/7/2022 |
| *Ligusticum chuanxiong* rhizome | Hong Kong, China | 20/7/2022 |
| *Lilium brownii* bulb | Hong Kong, China | 22/7/2022 |
| *Ophiopogon japonicus* root tuber | Hong Kong, China | 20/7/2022 |
| *Paeonia lactiflora* root | Hong Kong, China | 22/7/2022 |
| *Panax ginseng* root | Shandong, China | 14/5/2022 |

FIG. 5

| | | |
|---|---|---|
| *Platycodon grandiflorum* root | Hong Kong, China | 22/7/2022 |
| *Pueraria lobata* root | Hong Kong, China | 5/8/2022 |
| Raisins | Hong Kong, China | 10/8/2022 |
| Dried papaya | Hong Kong, China | 10/8/2022 |
| Corn starch | Hong Kong, China | 10/8/2022 |
| Dried star fruit | Hong Kong, China | 9/8/2022 |
| Dried mango | Hong Kong, China | 9/8/2022 |
| Snow fungus | Hong Kong, China | 9/8/2022 |
| Garlic | Hong Kong, China | 9/8/2022 |
| Onion | Hong Kong, China | 9/8/2022 |
| Cashew | Hong Kong, China | 10/8/2022 |
| *Citrus medica* fruit | Hong Kong, China | 22/7/2022 |
| *Crataegus pinnatifida* fruit | Hong Kong, China | 20/7/2022 |
| Dired banana | Hong Kong, China | 10/8/2022 |
| Dried blueberry | Hong Kong, China | 10/8/2022 |
| Dried figs | Hong Kong, China | 10/8/2022 |
| Dried kiwi | Hong Kong, China | 9/8/2022 |
| Dried longan pulp | Hong Kong, China | 5/8/2022 |
| Dired olives | Hong Kong, China | 9/8/2022 |
| *Lycium barbarum* fruit | Hong Kong, China | 20/7/2022 |
| Macadamia nut | Hong Kong, China | 10/8/2022 |
| *Prunus armeniaca* seed | Hong Kong, China | 22/7/2022 |
| Pistachios | Hong Kong, China | 10/8/2022 |
| *Pseudostellaria heterophylla* root | Hong Kong, China | 5/8/2022 |
| *Ziziphus jujuba* fruit | Hong Kong, China | 5/8/2022 |

FIG. 5 (Continued)

| RT (min) | Identification | Molecular formula | Ion species | Mean measured mass (Da) | Theoretical exact mass (Da) | Mass accuracy (ppm) | MS/MS fragments (*m/z*) (% abundance) | Reference |
|---|---|---|---|---|---|---|---|---|
| ***Ginger*** | | | | | | | | |
| 7.442 | 4-gingesulfonic acid | $C_{15}H_{22}O_6S$ | $[M-H]^-$ | 329.1038 | 329.1064 | 7.90 | 111.9277 (20.59), 80.9653 (53.69) | Wu et.al., 2018 |
| 8.495 | 6-gingesulfonic acid | $C_{17}H_{26}O_6S$ | $[M-H]^-$ | 357.1391 | 358.1465 | 4.05 | 181.0556 (100), 166.0283 (48.52), 139.0385 (29.98) | Wu et.al., 2018 |
| 9.750 | 8-gingesulfonic acid | $C_{19}H_{30}O_6S$ | $[M-H]^-$ | 385.1705 | 385.1690 | -3.89 | 303.2016 (32.81), 167.1459 (91.1) | Wu et.al., 2018 |
| ***Yam*** | | | | | | | | |
| 7.22 | 9-hydroxyoctadecadienoic acid sulfite | $C_{18}H_{32}O_6S$ | [M-H]- | 375.1841 | 375.1847 | 1.60 | 375.1841 (41.55), 295.2259 (100), 277.2138 (69.11), 191.0711 (49.19), 183.1359 (81.23) | Chan et.al., 2023 |
| ***Ginseng*** | | | | | | | | |
| 2.73 | 24-sulfonic-25-ene $Rg_1$ | $C_{42}H_{71}O_{17}S$ | $[M-H]^-$ | 879.4424 | 879.4412 | -1.36 | 879.4424 (100), 699.3752 (76.38) | Shen et.al., 2020 |
| 3.014 | 24-sulfonic-25-ene Re | $C_{48}H_{81}O_{21}S$ | $[M-H]^-$ | 1025.4985 | 1025.4991 | 0.59 | 1025.4985 (100), 845.4352 (25.94), 699.3765 (13.5) | Shen et.al., 2020 |
| 4.451 | 24-sulfonic-25-ene $Rg_2$ | $C_{42}H_{71}O_{16}S$ | $[M-H]^-$ | 863.4405 | 863.4463 | 1.26 | 863.4405 (100), 718.3563 (1.31), 537.326 (1.00) | Shen et.al., 2020 |
| 4.583 | 24-sulfonic-25-ene $Rg_2$ isomer | $C_{42}H_{71}O_{16}S$ | $[M-H]^-$ | 863.4403 | 863.4463 | 6.95 | 863.4403 (100), 537.326 (1.58) | Shen et.al., 2020 |
| 4.685 | 24-sulfonic-25-hydroxyl F1/Rh1 | $C_{36}H_{63}O_{13}S$ | $[M-H]^-$ | 735.3952 | 735.3989 | 5.03 | 735.3952 (100), 677.3512 (5.87), 555.328 (2.98) | Shen et.al., 2020 |
| 5.993 | $Rb_1$ sulfonate | $C_{54}H_{92}O_{26}S$ | $[M-H]^-$ | 1187.5505 | 1187.5525 | 1.68 | 1187.5505 (100), 1043.5239, (14.52), 845.4231 (78.51), 573.4344 (84.31) | |
| 6.872 | $Rb_1$ sulfonate isomer | $C_{54}H_{92}O_{26}S$ | $[M-H]^-$ | 1187.551 | 1187.5525 | 0.15 | 1187.5585 (100), 1142.5995 (80.98), 847.4499 (18.79) | |

FIG. 6

| Position | Tryptophan sulfonate | | Tryptophan | |
|---|---|---|---|---|
| | $\delta_C$, type (101 MHz) | $\delta_H$, mult (*J* in Hz, 400 MHz) | $\delta_C$, type (101 MHz) | $\delta_H$, mult (*J* in Hz, 400 MHz) |
| 1' | 174.2, C | | 174.5, C | |
| 2' | 55.0, CH | 3.93, m | 55.0, CH | 3.93, m |
| 3' | 25.4, $CH_2$ | 3.40, dd (15.1,8.4)<br>3.55, dd (15.1,5.0) | 26.3, $CH_2$ | 3.18, dd (15.2, 8.0)<br>3.36, dd (15.3, 4.8) |
| 2 | 135.3, C | | 125.0, CH | 7.19, s |
| 3 | 108.1, C | | 107.4, C | |
| 4 | 126.6, C | | 126.6, C | |
| 5 | 120.0, CH | 7.62, d (8.2) | 118.4, CH | 7.61, d (7.9) |
| 6 | 120.5, CH | 7.08, t (7.5) | 119.4, CH | 7.08, t (7.5) |
| 7 | 124.6, CH | 7.22, t (7.7) | 122.1, CH | 7.16, t (7.6) |
| 8 | 112.4, CH | 7.38, d (8.4) | 111.9, CH | 7.42, d (7.9) |
| 9 | 134.7, C | | 136.3, C | |

FIG. 7

| **Analyte** | **MRM** | **Collision Energy (eV)** | **Linearity** | | | **Sensitivity (mg/kg)** | | **Precision (RSD, %, n=6)** | | **Stability (RSD, %, n=8)** | **Spike recovery (RSD, %, n=3)** | | |
|---|---|---|---|---|---|---|---|---|---|---|---|---|---|
| | | | Range (µg/mL) | Equation | $R^2$ | LOQ | LOD | Inter-day | Intra-day | | Low | Middle | High |
| *UPLC-QqQ-MS/MS* | | | | | | | | | | | | | |
| Tryptophan sulfonate | 283.1→222.0 | 10 | 0.001-50 | y=169.262x+907.748 | 0.9999 | 0.002 | 0.001 | 3.30 | 2.26 | 4.50 | 108.20 (3.01) | 106.38 (4.82) | 104.79 (4.77) |
| Tryptophan | 203.1→116.0 | 10 | 1-100 | y=20.749x-50477.228 | 0.9993 | 0.117 | 0.039 | 2.17 | 1.67 | 1.88 | 91.76 (4.75) | 100.72 (2.76) | 108.53 (1.45) |
| *Acid-base titration* | | | | | | | | | | | | | |
| $SO_2$ residues | | | | | | 10.00 | | 6.08 | 8.77 | | 82.85 (1.79) | 84.99 (2.30) | 88.55 (3.90) |

METHODS FOR IDENTIFYING SULFUR-TREATED FOOD PRODUCTS

CROSS-REFERENCE TO RELATED APPLICATIONS

The present application claims priority from U.S. Provisional Patent Application No. 63/583,943, filed on Sep. 20, 2023, which is hereby incorporated by reference in its entirety.

STATEMENT REGARDING PRIOR DISCLOSURES BY THE INVENTORS OR JOINT INVENTORS UNDER 37 CFR 1.77(b)(6)

Part of the present invention was disclosed in a paper published in Yui-Man Chan, et al., Impact of Sulfur Fumigation on the Chemistry of *Dioscoreae Rhizoma* (Chinese Yam), ACS Omega 2023 8 (23), 21293-21304 DOI: 10.1021/acsomega.3c02729, available online May 30, 2023 and Kam-Chun Chan, et al., Tryptophan sulfonate: A new chemical marker for accurate and efficient inspection of sulfur-treated food products, *Food Chemistry*, Volume 434, 2024 doi: 10.1016/j.foodchem.2023.137360, available online Sep. 9, 2023. This paper is a grace period inventor-originated disclosure disclosed within one year before the filing date of this application and falls within the exceptions defined under 35 USC § 102(b)(1). These papers are hereby incorporated by reference in their entirety.

TECHNICAL FIELD

The present disclosure relates to analytical methods useful for identifying sulfur-treated food products.

BACKGROUND

Sulfur treatment, typically accomplished by sulfur fumigation or sulfite addition (e.g., sodium sulfate, sodium bisulfite, and sodium metabisulfite), is commonly utilized post-harvesting in the food industry worldwide. It is highly effective and relatively cheap, used for retaining moisture, preserving color and freshness, and preventing damage from insects and mold (Irwin et al., 2022). Despite these advantages, the practice has been challenged in view of its detrimental impacts on the quality of treated foods. Sulfur treatment can result in sulfite accumulation in treated products, which has been experimentally shown can induce respiratory symptoms, such as cough, chest tightness and throat irritation when these products are ingested (Mathison et al., 1985). Moreover, the treatment is capable of triggering irreversible qualitative and quantitative changes in various endogenous metabolites, such as saccharides (Zhou et al., 2016), vitamins (Ren et al., 2022), and saponins (Ma et al., 2017), which potentially degrades the inherent quality of treated foods. In agreement with this, several studies have provided evidence that sulfur fumigation or sulfite additives significantly reduce the nutritional value of treated food products (Ma et al., 2017; Ren et al., 2022). Even worse, long-term intake of sulfur-treated products may compromise liver and kidney functions (Jiang et al., 2020; Jiang et al., 2018a; Jiang et al., 2018b). Therefore, sulfur treatment has been strictly regulated to ensure that treated foods are safe to consume and that their beneficial properties are preserved.

To satisfy regulations, the inspection of sulfur-treated food products, i.e., identifying if a product has been sulfur-treated and determining the degree to which a product has been treated (e.g., the fumigation duration or the amount of sulfite additive), is required. Currently, sulfite assay is the only method available for the inspection (AOAC, 2019; U.S. Food and Drug Administration, 1986). In the assay, free and reversibly bound sulfites generated by sulfur treatment are chemically converted to either $SO_2$ or adducts by pH adjustment, distillation, or derivatization; the $SO_2$ and adducts are then quantified by titration, colorimetry, or liquid chromatography coupled with mass spectrometry (Robbins et al., 2015). The positive detection of sulfites indicates that the tested food sample was treated with sulfur; the more residual sulfites, the more intense the sulfur treatment. Although being applied universally, the sulfite assay suffers several drawbacks. First, false-positive results can present in some cases, such as members of the *Allium* genus (e.g., garlic and onion), as the plants are rich in endogenous sulfur-containing components (e.g., allicin) that can release sulfites under assay conditions (Carlos et al., 2020). Second, free and reversibly bound sulfites in sulfur-treated products are unstable and easily dissociated, such that the determined sulfite content may not represent the extent of sulfur treatment, or could give a false-negative result (Duan et al., 2016). Third, the experimental procedures involved in the assay, particularly in the sample pre-treatment (pH adjustment, distillation, or derivatization) and sulfite testing (titration or colorimetry), are complicated, laborious, and time-consuming with little automation. These factors further affect accuracy and block application in high-throughput analysis (Carlos and de Jager, 2017; Zhong et al., 2012).

There is thus a need for improved methods for detecting sulfur-treated food products that address at least some of the shortcomings in the art.

SUMMARY

In this study, we report a new chemical marker, namely tryptophan sulfonate, that can be used for the accurate and efficient inspection of sulfur-treated food products.

First, the chemical marker was discovered in three sulfur-fumigated products (ginger, yam, and ginseng) by ultra-performance liquid chromatography-quadrupole time-of-flight mass spectrometry (UPLC-QTOF-MS/MS)-based untargeted metabolomics. The identity of the chemical marker was then elucidated using chromatographic separation, nuclear magnetic resonance (NMR) analysis and chemical synthesis. Finally, to demonstrate its applicability in the inspection, a tryptophan sulfonate assay was developed using ultra-performance liquid chromatography-triple quadrupole mass spectrometry (UPLC-QqQ-MS/MS) to test 50 commercial food samples, in which the methodological superiority of the tryptophan sulfonate assay was highlighted, as compared to the sulfite assay, in terms of accuracy and efficiency.

In a first aspect, provided herein is a method of identifying a sulfur-treated food product, the method comprising: providing a sample comprising a food product; analyzing the sample using an analytical method to determine whether the sample comprises tryptophan sulfonate; and identifying based on whether the sample comprises tryptophan sulfonate that the food product is sulfur-treated, wherein the presence of tryptophan sulfonate indicates that the food product is sulfur-treated.

In certain embodiments, the analytical method comprises gas chromatography, liquid chromatography, thin layer chromatography, mass spectrometry, nuclear magnetic resonance, a stain, ultraviolet light absorption, or a combination thereof.

In certain embodiments, the method further comprises calculating a ratio of tryptophan sulfonate to tryptophan in the sample and determining based on the ratio of tryptophan sulfonate to tryptophan in the sample the intensity of sulfur treatment the food product was subjected to.

In certain embodiments, the step of analyzing the sample comprises analyzing the sample using a mass spectroscopy method thereby generating mass spectroscopy data and determining whether the mass spectroscopy data comprises one or more first markers indicative of the presence of tryptophan sulfonate.

In certain embodiments, the mass spectrometry method is tandem mass spectroscopy (MS/MS) and further comprises liquid chromatography.

In certain embodiments, the mass spectrometry method comprises high-performance liquid chromatography (HPLC-MS/MS) or ultra-performance liquid chromatography (UPLC-MS/MS).

In certain embodiments, the one or more first markers comprise an observed mass to charge ratio (m/z) selected from the group consisting of 283.04±0.01, 267.02±0.01, and 222.02±0.01 in negative ion mode or from the group consisting of 285.05±0.01, 146.06±0.01, and 118.06±0.01 in positive ion mode.

In certain embodiments, the mass spectroscopy method comprises multiple reaction monitoring (MRM) mode and the one or more first markers comprise an observed mass to charge ratio (m/z) of 283.04±0.01→222.02±0.01.

In certain embodiments, the step of analyzing the sample further comprises determining whether the mass spectroscopy data comprises one or second more markers indicative of the presence of tryptophan.

In certain embodiments, the one or more second markers comprise an observed mass to charge ratio (m/z) selected from the group consisting of 203.07±0.01 and 116.05±0.01.

In certain embodiments, the method further comprises calculating a ratio of tryptophan sulfonate to tryptophan in the sample and determining based on the ratio of tryptophan sulfonate to tryptophan in the sample the intensity of sulfur treatment the food product was subjected to.

In certain embodiments, the method further comprises extracting the food product with a solvent thereby forming the sample.

In certain embodiments, the solvent comprises an alcohol and optionally water.

In certain embodiments, the solvent comprises at least one of methanol and ethanol and optionally water.

In certain embodiments, the food product comprises a fruit, a tuber, a vegetable, a fungi, a nut, a legume, a cereal, a rhizome, a meat, an egg, a seafood, a traditional Chinese medicine, or a mixture thereof.

In certain embodiments, the food product comprises a fruit, a tuber, a vegetable, a fungi, a nut, a legume, a cereal, a rhizome, or a mixture thereof.

In certain embodiments, the food product comprises *Amomum kravanh* fruit, *Anemarrhena asphodeloides* rhizome, *Angelica dahurica* root, *Angelica sinensis* root, *Atractylodes macrocephala* rhizome, *Aletilla striata* tuber, *Codonopsis pilosula* root, *Dioscorea opposita* rhizome, apple, apricot, ginger, guava, peach, pear, pineapple, potato, strawberry, *Gastrodia elata* tuber, *Glehnia littoralis* root, *Glycyrrhiza uralensis* root, *Ligusticum chuanxiong* rhizome, *Lilium brownii* bulb, *Opphiopogon japonicus* root tuber, *Paeonia lactiflora* root, *Panax ginseng* root, *Platycodon grandiflorum* root, *Pueraria lobata* root, grape, papaya, starch, star fruit, mango, snow fungus, garlic, onion, cashew, *Citrus medica* fruit, *Crataegus pinnatifida* fruit, banana, blueberry, fig, kiwi, longan pulp, olives, *Lycium barbarum* fruit, macadamia nut, *Prunus armeniaca* seed, pistachios, *Pseudostellaria heterophylla* root, *Ziziphus jujuba* fruit, or a mixture thereof.

In certain embodiments, the sulfur-treated food product was treated with sulfur-fumigation, sodium sulfate, sodium bisulfite, sodium metabisulfite, or a mixture thereof.

In a second aspect, provided herein is a method of identifying a sulfur-treated food product, the method comprising: providing a sample comprising a food product;

analyzing the sample using an analytical method selected from the group consisting of high-performance liquid chromatography (HPLC-MS/MS) and ultra-performance liquid chromatography (UPLC-MS/MS) thereby generating mass spectroscopy data;

determining whether the mass spectroscopy data comprises one or more first markers indicative of the presence of tryptophan sulfonate, wherein the one or more first markers comprise an observed mass to charge ratio (m/z) selected from the group consisting of 283.04±0.01, 267.02±0.01, and 222.02±0.01; and identifying based on whether the mass spectroscopy data comprises the one or more first markers indicative of the presence of tryptophan sulfonate that the food product is sulfur-treated, wherein the presence of one or more first markers indicative of the presence of tryptophan sulfonate indicates that the food product is sulfur-treated.

In certain embodiments, the food product comprises a fruit, a tuber, a vegetable, a fungi, a nut, a legume, a cereal, a rhizome, a meat, an egg, a seafood, or a mixture thereof.

BRIEF DESCRIPTION OF THE DRAWINGS

The foregoing aspects and many of the attendant advantages of this invention will become more readily appreciated and understood by reference to the following detailed description, when taken in conjunction with the accompanying drawings.

FIG. 5 depicts Table 1 showing information of 50 commercial food products

FIG. 6 depicts Table 2 showing molecular features of the sulfur derivatives identified in ginger, yam, and ginseng by UPLC-QTOF-MS/MS.

FIG. 7 depicts Table 3 showing $^1H$ NMR and $^{13}C$ NMR data of tryptophan sulfonate and tryptophan in $D_2O$.

FIG. 8 depicts Table 4 showing method validation for quantitative assays.

DETAILED DESCRIPTION

Definitions

Figure 1:
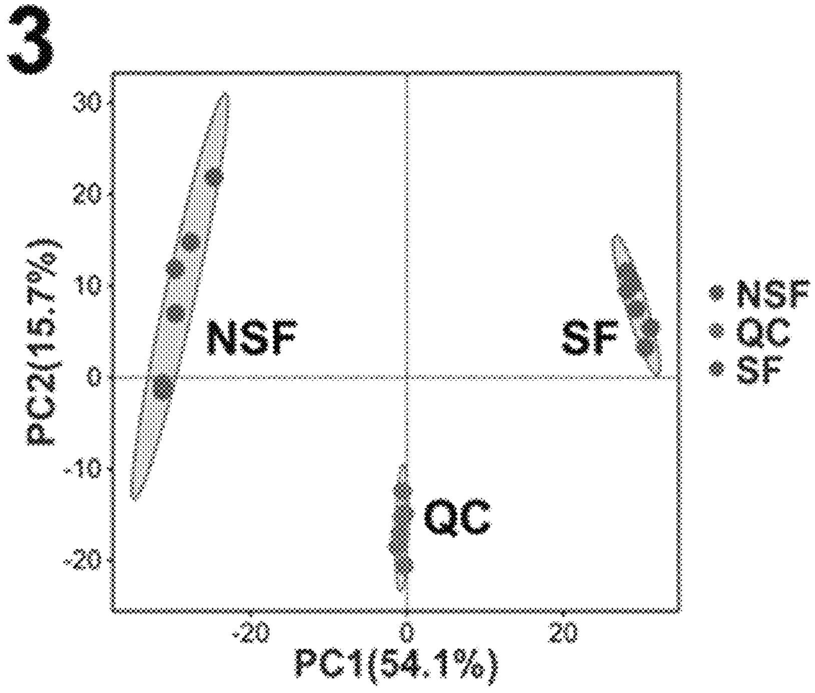
FIG. 1 depicts PCA score plots (A), volcano plots (B), and selected ion (m/z 283.04) chromatograms (C) of sulfur-fumigated (SF) and non-sulfur-fumigated (NSF) ginger (1), yam (2), and ginseng (3) samples by UPLC-QTOF-MS/MS-based untargeted metabolomics.
Figure 1:
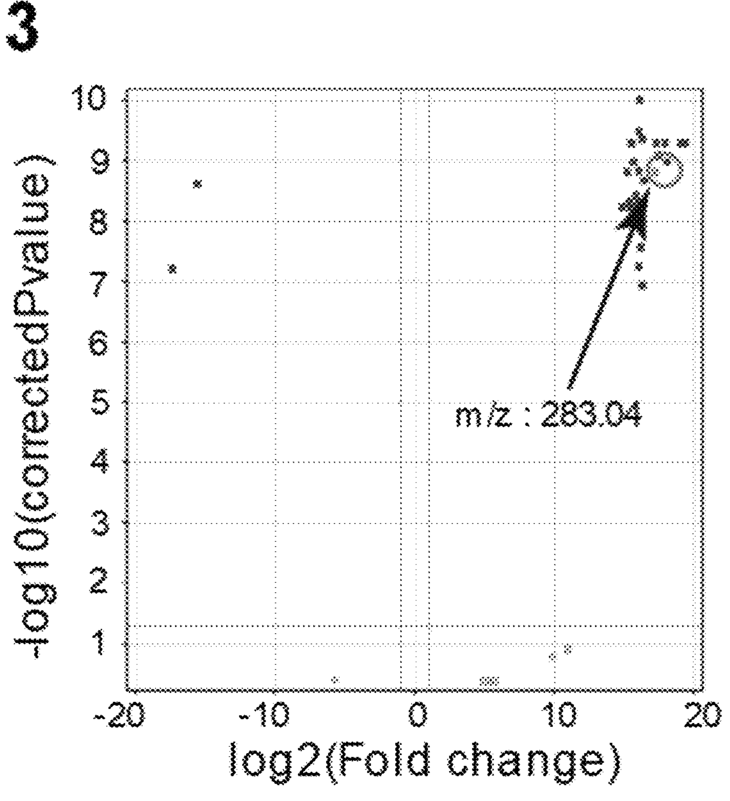

The following terms shall be used to describe the present invention. In the absence of a specific definition set forth herein, the terms used to describe the present invention shall be given their common meaning as understood by those of ordinary skill in the art.

Throughout the present disclosure, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present disclosure and claims, unless the context requires otherwise, the word "include" or variations such as "includes" or "including", will be understood to imply the inclusion of a stated integer or group of integers, but not the exclusion of any other integer or group of integers.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

As used herein, the term "tryptophan sulfonate refers to a compound having the chemical formula $C_{11}H_{12}N_2O_5S$ or a conjugate salt or zwitterion thereof. In certain embodiments, tryptophan sulfonate can be represented having the formula:

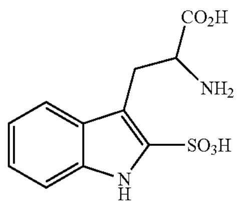 [SMILES: NC(Cc1c(S(=O)(=O)O)[nH]c2ccccc12)C(=O)O]

or a conjugate salt or zwitterion thereof.

The term "food product" as used herein refers to any product intended for consumption by a subject.

As used herein, the term "subject" refers to any animal (e.g., a mammal), including, but not limited to, humans, non-human primates, canines, felines, and rodents.

The present disclosure provides a method of identifying a sulfur-treated food product, the method comprising: providing a sample comprising a food product; analyzing the sample using an analytical method to determine whether the sample comprises tryptophan sulfonate; and identifying based on whether the sample comprises tryptophan sulfonate that the food product is sulfur-treated, wherein the presence of tryptophan sulfonate indicates that the food product is sulfur-treated.

Any analytical method that is capable of selectively detecting tryptophan sulfonate can be used in the methods described herein. The selection of the appropriate analytical method is well within the skill of a person of ordinary skill in the art. In certain embodiments, the analytical method comprises gas chromatography, liquid chromatography, thin layer chromatography, mass spectrometry, nuclear magnetic resonance, a stain (e.g., a chemical stain or labeled antibody), ultraviolet light absorption, or a combination thereof. In certain embodiments, the analytical method comprises mass spectrometry.

Mass spectrometry can be performed using a mass spectrometer comprising an ion source for ionizing the sample and creating charged molecules and/or charged fragments for further analysis. The ionization of the sample can be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. A person of ordinary skill in the art will understand that the choice of ionization method can be determined based on the properties of the analyte(s) being measured, type of sample, detector type, the choice of positive versus negative mode, etc. The ionizer can operate in positive or negative ion mode. In certain embodiments, the ionization of the sample is accomplished using ESI.

Once the sample has been ionized, the positively charged or negatively charged ions thereby created may be analysed to determine an m/z ratio. Exemplary analysers for determining m/z ratios include, but are not limited to, quadrupole analysers, ion traps analysers, and time-of-flight (TOF) analysers. In certain embodiments, the analyser is a tandem mass spectrometers (MS) selected from a triple quadrupole MS and 2 dual-focusing; and hybrid MS selected from the group consisting of quadrupole TOF (Q-TOF), ion trap TOF (IT-TOF), quadrupole ion trap (Q-IT), quadrupole-cyclotron-resonance (Q-ICR), ion trap ion-cyclotron-resonance (IT-ICR), ion trap orbitrap (IT-orbitrap), 2 TOF (TOF-TOF), and multistage MS ($MS^n$). The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). In certain embodiments, the m/z ratio is determined using a Q-TOF analyser.

The m/z data generated as a result of the mass spectrometry analysis of the sample can then be examined to determine whether the sample comprises ions that are indicative of the presence of tryptophan sulfonate and/or tryptophan sulfonate fragment ions in the sample. In embodiments in which the mass spectrometry method is conducted in negative ion mode, the one or more markers can comprise an observed mass to charge ratio (m/z) selected from the group consisting of 283.04±0.01, 267.02±0.01, and 222.02±0.01. In embodiments in which the mass spectrometry method is conducted in positive ion mode, the one or more markers can comprise an observed mass to charge ratio (m/z) selected from the group consisting of 285.05±0.01, 146.06±0.01, and 118.06±0.01.

In certain embodiments, the mass spectrometry method further comprises liquid chromatograph prior to the step of analysing the hydrolysate of the sample by mass spectrometry. Liquid chromatography is a process involving at least partial obstruction of one or more components of a fluid solution (mobile phase) as the mobile phase passes through a column of a substance, through capillary passageways, or through a single contiguous column of solid support, such as monolithic column. The at least partial obstruction results from the distribution of the components of the mixture between the stationary phase and mobile phase, as this mobile phase moves relative to the stationary phase(s). Examples of liquid chromatography include, but are not limited to, HPLC, UPLC [also known as ultrahigh performance liquid chromatograph (UHPLC)], and reverse phase liquid chromatography (RPLC). In certain embodiments, the mass spectrometry method further comprises HPLC or UPLC, such as HPLC-MS, UPLC-MS, HPLC-MS/MS or UPLC-MS/MS. In the examples below the mass spectrometry method comprises reverse phase UPLC-ESI-qTOF-MS/MS using a C18 column.

In instances in which the mass spectrometry method further comprises liquid chromatography, the method can further comprise determining whether the liquid chromatography spectrum comprises a peak with a retention time that is indicative of the presence of tryptophan sulfonate by comparing a predicted liquid chromatography retention time of tryptophan sulfonate, wherein the predicted liquid chromatography retention time of tryptophan sulfonate is determined by measuring the retention time of a standard sample comprising tryptophan sulfonate. The retention time of the standard sample comprising tryptophan sulfonate can be measured under substantially similar liquid chromatography parameters as the sample. Such parameters can include, but are not limited to, column/solid media type, mobile phase solvent(s), mobile phase flow rate, pressure, temperature, and the like. The selection of liquid chromatography parameters is well within the skill of a person of ordinary skill in the art.

In certain embodiments, the analytical method comprises UPLC-QTOF-MS/MS, wherein the ionization of the sample is accomplished using ESI.

The food product is not particularly limited and can be any food or naturally occurring medicament or mixture of naturally occurring medicaments (e.g., traditional Chinese medicine or herbal medicine). In certain embodiments, the food product is a fruit, a tuber, a vegetable, a fungi, a nut, a legume, a cereal, a rhizome, a meat, poultry, an egg, a seafood or a mixture thereof. The food product may be natural, processed, and/or a mixture of different food products.

Exemplary food products include, but are not limited to, food product comprises *Amomum kravanh* fruit, *Anemarrhena asphodeloides* rhizome, *Angelica dahurica* root, *Angelica sinensis* root, *Atractylodes macrocephala* rhizome, *Aletilla striata* tuber, *Codonopsis pilosula* root, *Dioscorea opposita* rhizome, apple, apricot, ginger, guava, peach, pear, pineapple, potato, strawberry, *Gastrodia elata* tuber, *Glehnia littoralis* root, *Glycyrrhiza uralensis* root, *Ligusticum chuanxiong* rhizome, *Lilium brownii* bulb, *Opphiopogon japonicus* root tuber, *Paeonia lactiflora* root, *Panax ginseng* root, *Platycodon grandiflorum* root, *Pueraria lobata* root, grape, papaya, starch, star fruit, mango, snow fungus, garlic, onion, cashew, *Citrus medica* fruit, *Crataegus pinnatifida* fruit, banana, blueberry, fig, kiwi, longan pulp, olives, *Lycium barbarum* fruit, macadamia nut, *Prunus armeniaca* seed, pistachios, *Pseudostellaria heterophylla* root, *Ziziphus jujuba* fruit, and mixtures thereof.

The sulfur-treated food product can result in any method of sulfur treatment including, but not limited to treatment with sulfur-fumigation, sodium sulfate, sodium bisulfite, sodium metabisulfite, or a combination thereof.

The food product can be intended for consumption by a human or a non-human mammal, such as a dog, cat, horse, cow, goat, chicken, pig, or fish.

The sample comprising the food product can be prepared according to any method known in the art. In certain embodiments, the food product is extracted with a solvent thereby forming the sample. The solvent used to extract the food product can be any solvent in which tryptophan sulfonate is at least partially soluble. The selection of the appropriate solvent is well within the skill of a person of ordinary skill in the art. In certain embodiments, the solvent comprises an alcohol (e.g., a $C_1$-$C_6$ alcohol, $C_1$-$C_5$ alcohol, $C_1$-$C_4$ alcohol, $C_1$-$C_3$ alcohol, or $C_1$-$C_2$ alcohol), acetonitrile, nitromethane, dimethyl sulfoxide, dimethyl formamide, acetone, chloroform, ethylene glycol, 1,2-propandiol, glycerol, and super critical carbon dioxide. In certain embodiments, the solvent further comprises water. In certain embodiments, the solvent comprises one or more of methanol and ethanol and optionally water.

In certain embodiments, the food product is subjected to one or more optional steps including washing, dehydrating, and powderizing, e.g., by cutting, tearing, breaking, pulverizing, shredding, and/or any other mechanical size reduction technique.

Untargeted Metabolomics

The UPLC-QTOF-MS/MS data were processed by principal component analysis (PCA) to investigate the chemical profile differences between sulfur-fumigated and non-fumigated samples of ginger, yam, and ginseng. For each species, chromatographic peaks from 18 data sets of samples (6 sulfur-fumigated samples, 6 non-fumigated samples, and 6 QC samples) were first subjected to MetaboAnalyst for data processing. All data features after data filtering were then imported to OmicShare tool for PCA, and the results were presented as score plots to show the degree of clustering or dispersion between different sample groups by reducing the dimensionality of the data sets. As shown in the PCA score plots (FIG. 1A), all the samples fell well into the 95% tolerance region of confidence level. For the PCA models of three cases, all $R^2X$ (cum.) and $Q^2$ (cum.) with five components were higher than 0.80 and 0.54, respectively. Based on the criteria of $R^2X$ (cum.) close to 1 and $Q^2$ (cum.) greater than 0.5 and their difference within 0.2, the PCA modelling shows a good fit and satisfactory predictive ability (Peng et al., 2020). The score plots of PCA showed that the sulfur-fumigated and non-fumigated samples were clearly clustered into two groups in all of three case studies, which demonstrated that the sulfur treatment significantly changed the chemical profiles of small metabolites in ginger, yam, and ginseng.

The volcano plot analysis was then applied to identify the specific components that are responsible for the chemical differences between sulfur-fumigated and non-fumigated samples. Shown on the right of the volcano plots (FIG. 1B), all mass ions with positive fold changes >3 by the sulfur treatment were targeted (Talib et al., 2019). Among them, multiple molecular features of sulfur-containing derivatives were exclusively observed in the three fumigated samples, which is in agreement with previous studies (Wu et al., 2018; Chan et al., 2023; Shen et al., 2020). As summarized in Table 2 (FIG. 6), these derivatives were identified based on their MS/MS data, mostly related to an addition of —$SO_3H$ group to specific types of compounds in the samples, such as shogaols in ginger, linoleic acid in yam, and ginsenosides in ginseng. Interestingly, an ion at m/z 283.04 for $[M-H]^-$ was found as a shared feature of all the sulfur-fumigated groups, contributing to the chemical differences between sulfur-fumigated and non-fumigated groups. By comparing chromatograms of the tested samples, it was further found that the ion was exclusively detected in sulfur-fumigated samples but not in non-fumigated samples (FIG. 1C). In other words, the compound corresponding to the ion was an artificial derivative generated by the sulfur treatment and distributed in all three sulfur fumigated products. This consistent pattern suggests this ion as an exclusive and universal chemical marker of sulfur-treated products.

Chemical Identity Elucidation

MS Analysis

Next, the chemical identity of the compound was explored according to its MS data. In negative ion mode, it produced a pseudo-molecular ion peak at m/z 283.0405 for $[M-H]^-$, which corresponded to the molecular formula of $C_{11}H_{11}N_2O_5S$. The MS/MS spectrum (FIG. 2A) showed fragment ions at m/z 267.0158, 222.0233, 142.0662, and 116.0522, indicating losses of a hydroxyl group (—OH, m/z 17 Da) and a carboxyl group with an amine group (—COOH—$NH_3$, m/z 62 Da) from the original compound. Moreover, an abundant fragment ion at m/z 142.0657 was found and proposed to be generated through the loss of a sulfur trioxide radical anion (—$SO_3$, m/z 80 Da) from the ion at m/z 222.02226 (Jariwala et al., 2012). By comparing the MS data with those of tryptophan, the compound was tentatively identified as a sulfur derivative of tryptophan.

NMR Analysis

Figure 2:
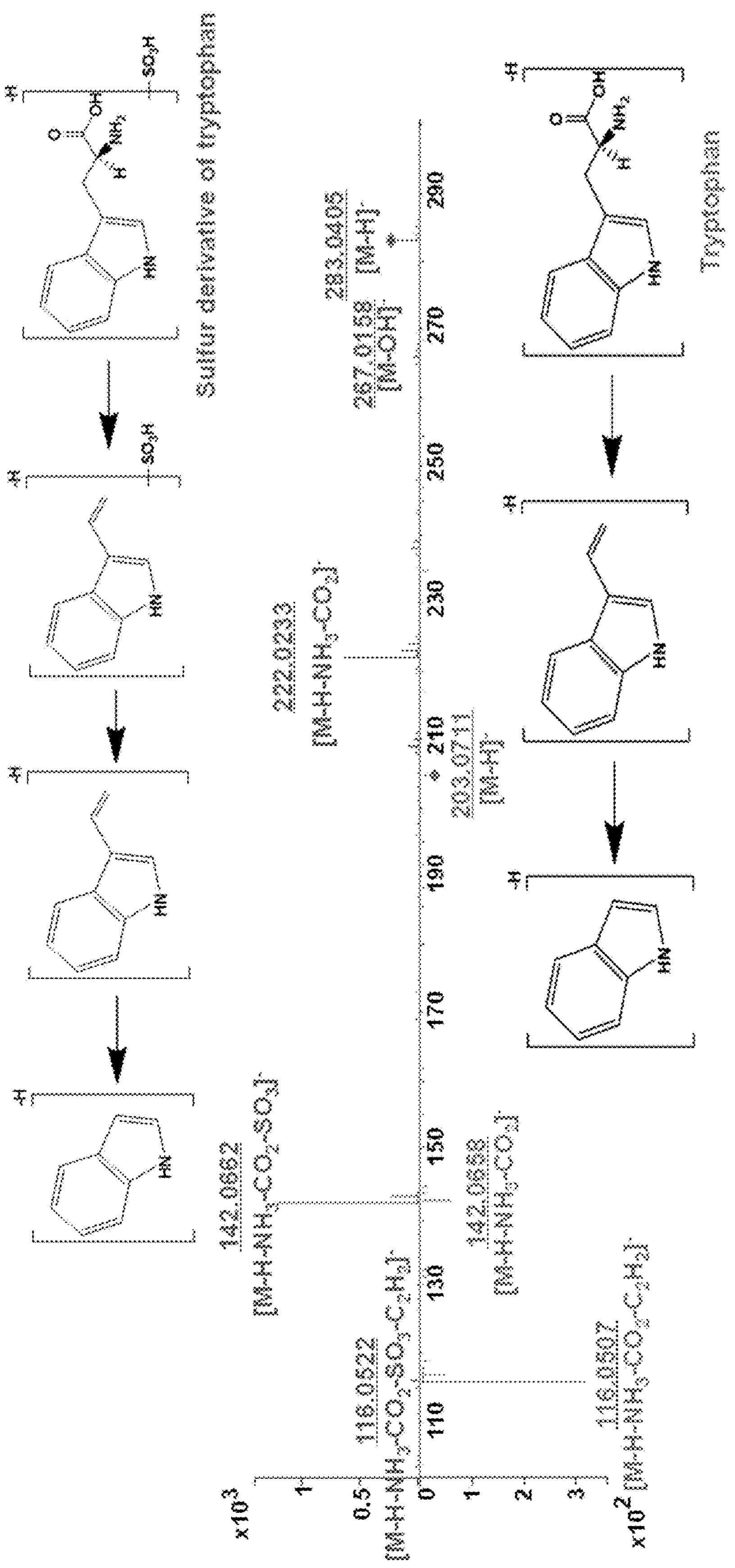
FIG. 2 depicts MS/MS spectrum of tryptophan and its sulfur derivative (A) and proposed chemical transformation of tryptophan sulfonate from tryptophan (B).

For further structural elucidation, the compound was isolated from the sulfur-fumigated ginger and then analyzed by NMR (Table 3, FIG. 7). The $^1H$ NMR spectrum of the compound in $D_2O$ (FIG. S1A) exhibited signals corresponding to one methylene group [$\delta_H$ 3.40 (dd, J=15.1, 8.4 Hz), 3.55 (dd, J=15.1, 5.0 Hz)], one methine group [$\delta_H$ 3.93 (m)] and four aromatic protons [$\delta_H$ 7.08 (t, J=7.5 Hz), 7.22 (t, J=7.7 Hz), 7.38 (d, J=8.4 Hz), 7.62 (d, J=8.2 Hz)]. Its $^{13}C$ and HSQC NMR spectra (FIGS. S1B & C) showed 11 carbon signals with the configuration of one methylene, one methine with a nitrogen-containing group ($\delta_c$ 55.0), one carboxylic acid ($\delta_c$ 174.2), and one heteroaromatic ring with four quaternary carbons ($\delta_c$ 108.1, 126.6, 134.7, 135.3), and four tertiary carbons ($\delta_c$ 112.4, 120.0, 120.5, 124.6). The structural linkage was further verified by $^1H$-$^1H$ COSY and HMBC analysis. In the $^1H$-$^1H$ COSY analysis (FIG. S1D), two proton-spin systems were shown by the correlations from (a) H-2'/H-3', as well as the multi-correlations from (b) H-5/H-6/H-7/H-8. In the HMBC analysis (FIG. S1E), two systems were linked through the C-3 due to the correlations with H-5 ($\delta_H$ 7.62) to C-3 ($\delta_c$ 108.1) and from H-2'/$H_2$-3' ($\delta_H$ 3.93, 3.40, 3.55) to C-3 ($\delta_c$ 108.1). All the NMR data support the structural similarity of the compound with tryptophan. However, compared to the spectra of tryptophan, the disappearance of a signal of H-2 [$\delta_H$ 7.19 (s)] and certain deshielding effects in $H_2$-3' shifting from [$\delta_H$ 3.18 (dd), 3.36 (dd)] to [$\delta_H$ 3.40 (dd), 3.55 (dd)] were observed in the $^1H$ NMR spectrum of the targeted compound (FIG. S2A). Moreover, its $^{13}C$ NMR spectrum shows C-2 shifting from ($\delta_c$ 125.0) to ($\delta_c$ 135.3), indicating deshielding (FIG. S2B). The variations indicate that the compound is a structural analogue of tryptophan in which a proton at position 2 was replaced by a sulfo group. Therefore, the compound was structurally confirmed as tryptophan sulfonate (2'-amino-3' (2-sulfo-1H-indol-3yl) propanoic acid) (FIG. 2B).

Chemical Synthesis

Having identified tryptophan sulfonate consistently appearing associated with sulfur-fumigated products, we next investigated how it was being produced. We propose that tryptophan sulfonate is generated from endogenous tryptophan in food by sulfur fumigation. Tryptophan is exclusively produced by plants and microorganisms through a series of enzymatic reactions known as tryptophan synthase (Chen et al., 2018; Radwanski & Wutzke, 1995). Tryptophan is typically found in most animal- and plant-based proteins and is therefore abundant in protein-rich foods (Friedman, 2018; Heine & Wutzke, 1995). During sulfur fumigation, sulfur is burned and reacts with oxygen to produce $SO_2$. It then combines with water on the surface of the foods to generate $H_2SO_3$ or other types of sulfites, which disassociate into $HSO_3$—. The nucleophilic properties of $HSO_3$− are relatively strong due to the presence of a lone pair of electrons on the sulfur atom, which readily interacts with electrophilic species, allowing for effective nucleophilic attacks (Zhang et al., 2022). Without wishing to be bound by theory, it is believed that the chemical mechanisms underlying the generation of tryptophan sulfonate could involve the nucleophilic addition of $HSO_3^-$ to C-2 of tryptophan, a potential electrophilic site, and subsequent deprotonation (removal of a hydrogen ion), thereby regenerating an aromatic indole ring (FIG. 2B). For further confirmation of the transformation mechanism, a method of chemical synthesis was developed that allows tryptophan to react with $NaHSO_3$ in water. Then, purifying the synthetic residue by macroporous resin and semi-prep-HPLC produced the desired compound (40.2 mg, yield 4.02%). The chemical structure of the compound was verified as tryptophan sulfonate by mass spectroscopy and NMR, and the purity>98% was determined by peak area normalization. The successful synthesis of tryptophan sulfonate from tryptophan provides evidence for our hypothesis that tryptophan sulfonate is a sulfur treatment-induced derivative of tryptophan.

Tryptophan Sulfonate Assay

Method Validation

The quantitative assay of tryptophan sulfonate and tryptophan was validated in terms of linearity, LODs, LOQs, intra- and inter-day precision, stability, and recovery which the results are summarized in Table 4 (FIG. 8). Calibration curves displayed good linearity ($R^2$>0.999) over a broad range of concentrations, indicating that it was able to quantify the analytes in diverse types of samples. The LODs and LOQs for tryptophan sulfonate were 0.001 and 0.002 μg/mL, respectively, while those for tryptophan were 0.039 and 0.117 μg/mL. The RSDs of intra- and inter-day precision ranged from 1.67 to 3.30%. The stability of tryptophan sulfonate and tryptophan exhibited RSDs of 4.50% and 1.88%, respectively. The average recoveries of tryptophan sulfonate and tryptophan were between 91.76% and 108.53% with RSD of less than 5%. All these results proved that our established assay was sensitive, precise, accurate, and stable enough for the quantitative assay of tryptophan sulfonate and tryptophan in food products (Qi et al., 2022).

Specificity to Sulfur-Treated Products

To further validate the specificity of tryptophan sulfonate to sulfur-treated products, comparative experiments on an additional set of 20 food products were conducted by the tryptophan sulfonate assay. The results (FIG. 3A) indicate that tryptophan sulfonate was present in all sulfur-fumigated samples (ranging from 0.25 to 15.67 mg/kg), while it was not detected in the non-fumigated samples. This finding provides stronger evidence that sulfur treatment results in the generation of tryptophan sulfonate, which is absent in the non-treated samples.

Figure 3:
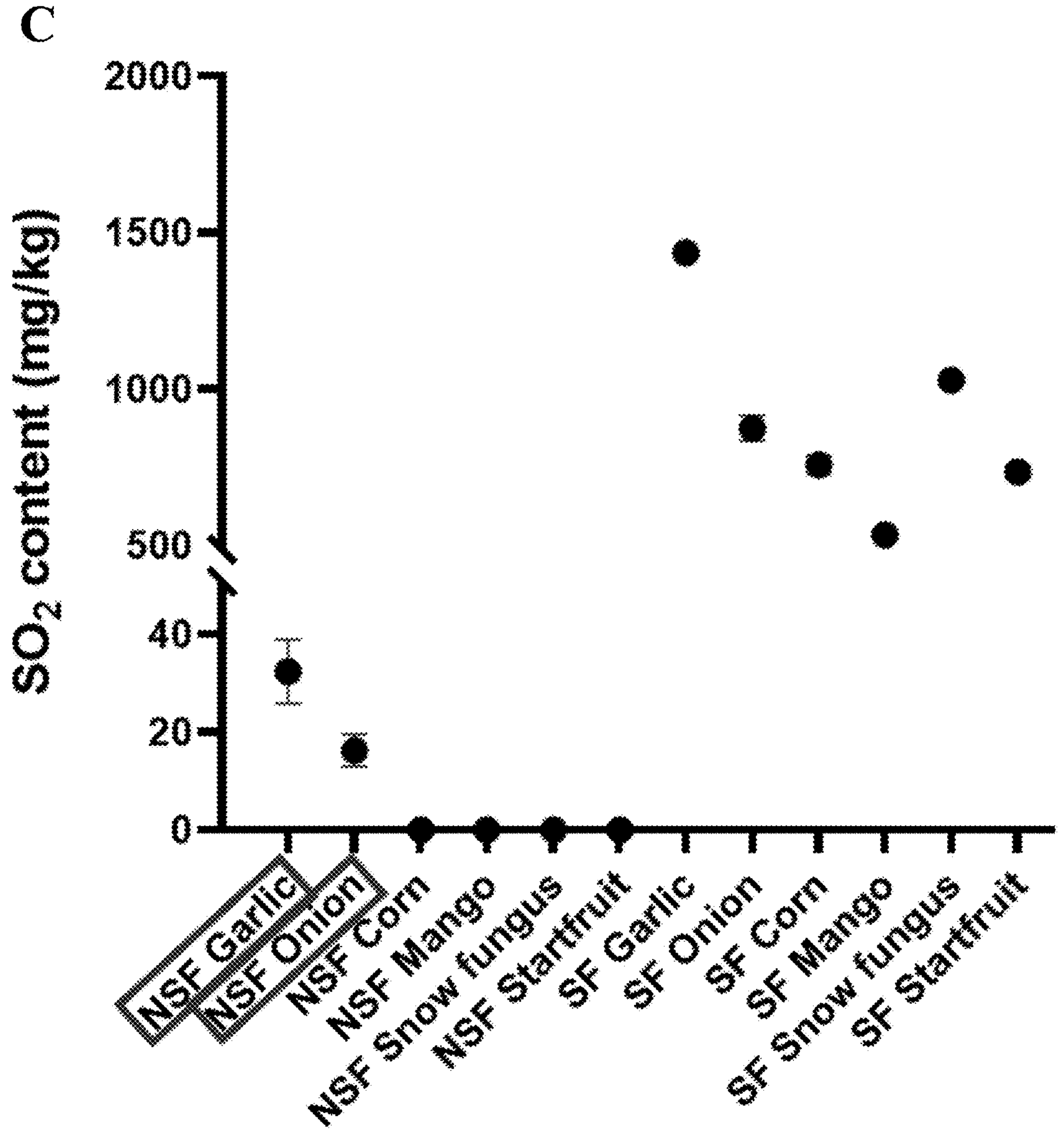
FIG. 3 depicts content of tryptophan sulfonate in 20 sulfur-treated and non-treated food samples (A), the contents of tryptophan sulfonate, tryptophan, and $SO_2$ in 50 commercial food samples (B), and the content validation of $SO_2$ in 6 self-prepared food samples (C).

We then tested 50 commercial food samples randomly collected from markets by the tryptophan sulfonate assay to demonstrate the applicability of tryptophan sulfonate as a specific chemical marker for determining whether products had been treated with sulfur. The results (FIG. 3B) show that tryptophan sulfonate was detected in 33 samples with contents varying from 0.008 to 168.03 mg/kg, while tryptophan was detected in 49 samples from 24.34 to 173.89 mg/kg. Given the high specificity of tryptophan sulfonate, we postulate that the samples containing tryptophan sulfonate had been sulfur-treated, and the others not. The determination of $SO_2$ residues was also performed on the commercial samples. The results obtained by the tryptophan sulfonate assay and sulfite assay were largely identical except for six samples, namely corn starch, dried star fruit, dried mango, snow fungus, garlic, and onion. Among them, garlic and onion were found to have $SO_2$, but not tryptophan sulfonate; while corn starch, dried star fruit, dried mango, and snow fungus were found to have tryptophan sulfonate but not $SO_2$. As garlic and onion belong to the *Allium* family, known to contain intrinsic sulfur-containing constituents, false-positive results from the sulfite assay are reasonable (Carlos et al., 2020). We speculate that the other four samples tested false-negative in the sulfite assay due to the instability of free and reversibly bound sulfites (Xu et al., 2018). To verify this, we determined $SO_2$ in the sulfur-treated and non-treated samples of these six products (FIG. 3C). It was found that, in the cases of garlic and onion, $SO_2$ was detected in all samples, but tryptophan sulfonate was detected only in the sulfur-treated samples. As for the other four samples, neither $SO_2$ nor tryptophan sulfonate was detected in the naturally dried samples, but both were detected in the sulfur-treated samples. The findings further evidenced the inaccuracy, i.e., false-positive and false-negative results, of the sulfite assay. However, the tryptophan sulfonate assay consistently gave accurate results. All the facts demonstrate that, compared to $SO_2$, tryptophan sulfonate is more specific as a characteristic chemical marker and therefore is more accurate for the inspection of sulfur fumigation. The presence of tryptophan is prerequisite for this test. As previously mentioned, tryptophan exits in most foods (Friedman, 2018). In this study, tryptophan was found in 49 of the 50 commercial samples. The one sample in which it was not found was dried papaya. Interestingly, both tryptophan sulfonate and $SO_2$ were detected in the sample. We therefore suspect that tryptophan had originally existed in the papaya sample but was completely transformed into tryptophan sulfonate by sulfur treatment.

Stability During and after Sulfur Treatment

Figure 4:
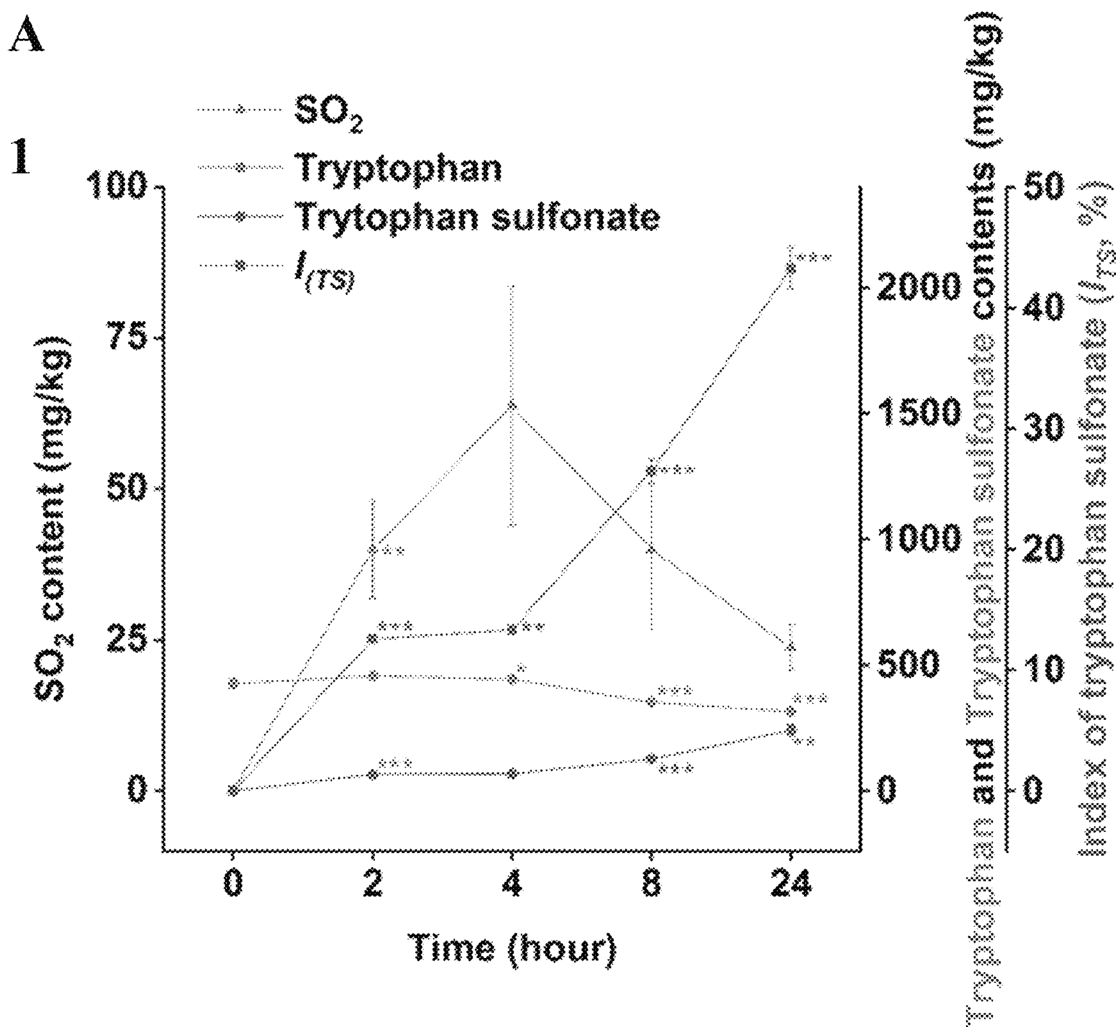
FIG. 4 depicts content variations by 24 h sulfur fumigation (A), 48 h short-term heating processing and 9-month long-term storage (B), PCA score plots (C), in which the lines showing the quality variation of samples between 0 h and each time-point and heatmap (D) showing the correlation between the related parameters in ginger (1), yam (2), and ginseng (3). * $p<0.001$,  $p<0.01$, compared with the first time-point, e.g., 0th h or 1st month. ###$p<0.001$, #$p<0.05$, compared with the 2nd h in yam and 4th h in ginseng and ginger. ^^$p<0.01$; ^$p<0.05$ in heatmap analysis.
Figure 4:
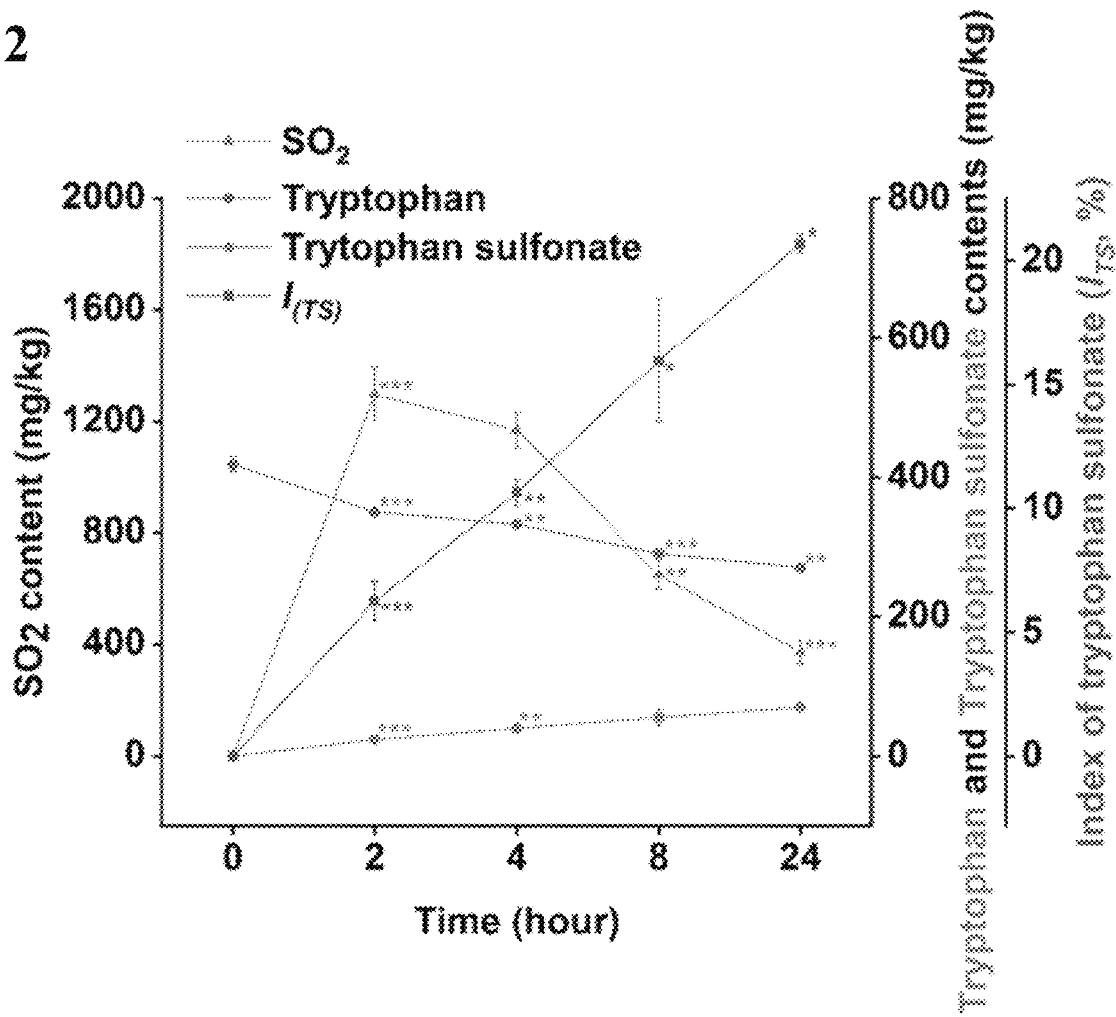
Figure 4:
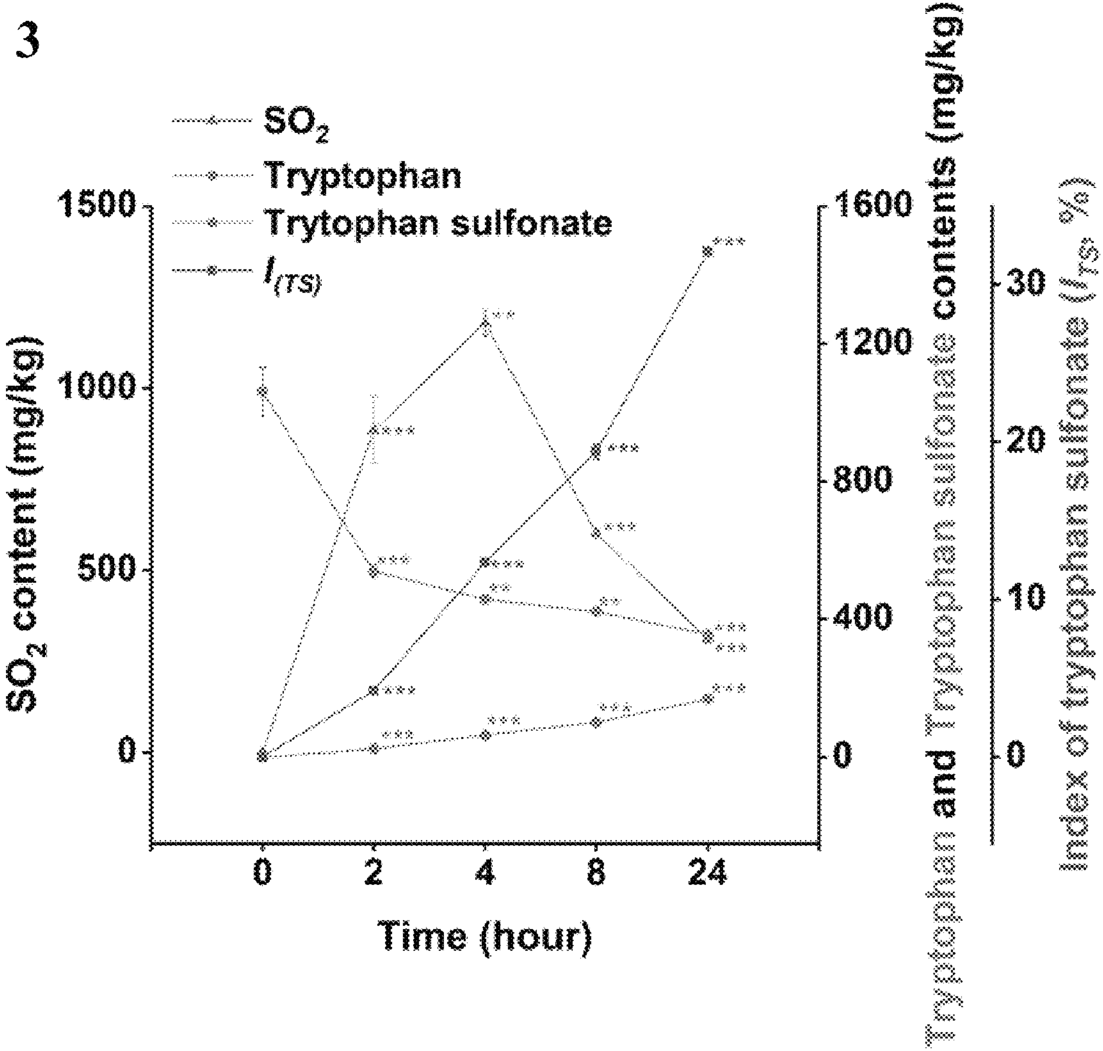
Figure 4:
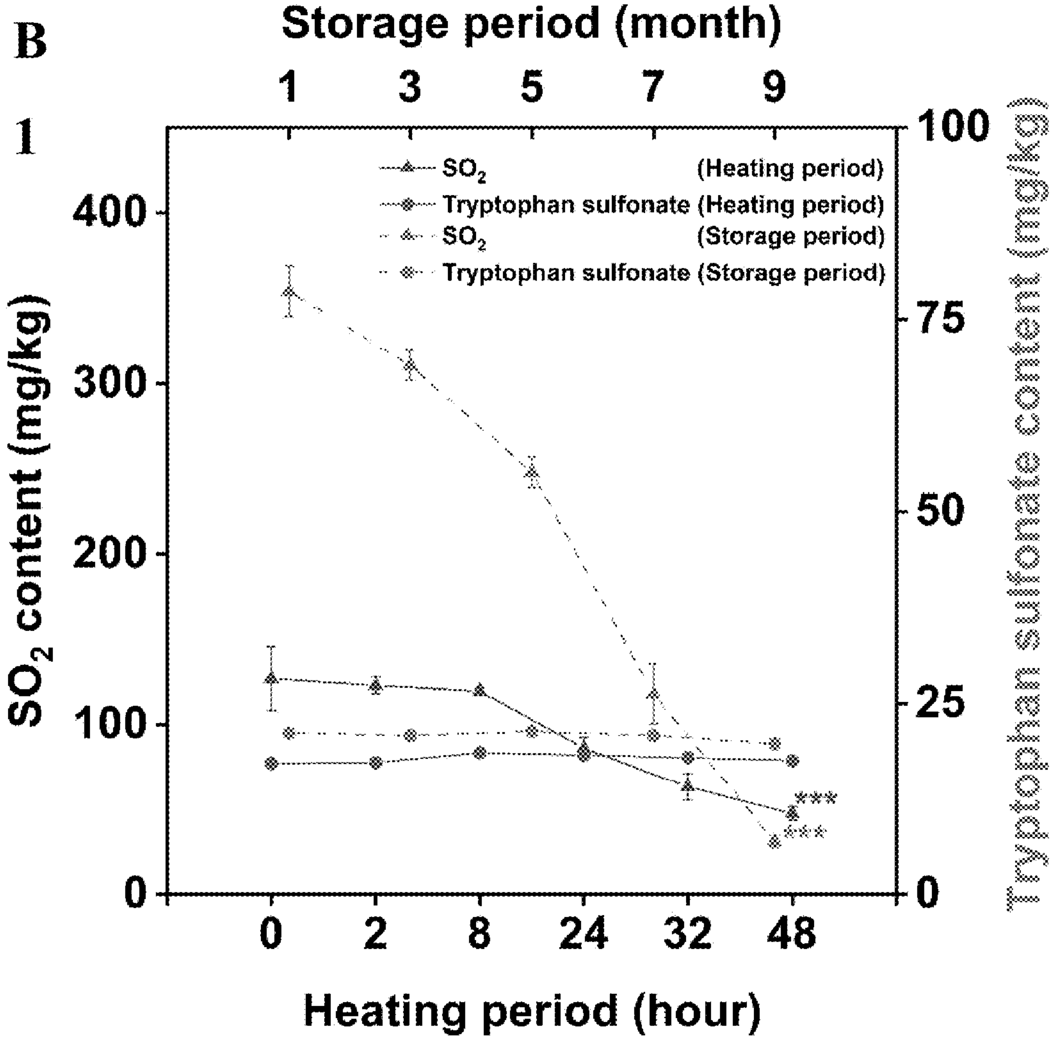
Figure 4:
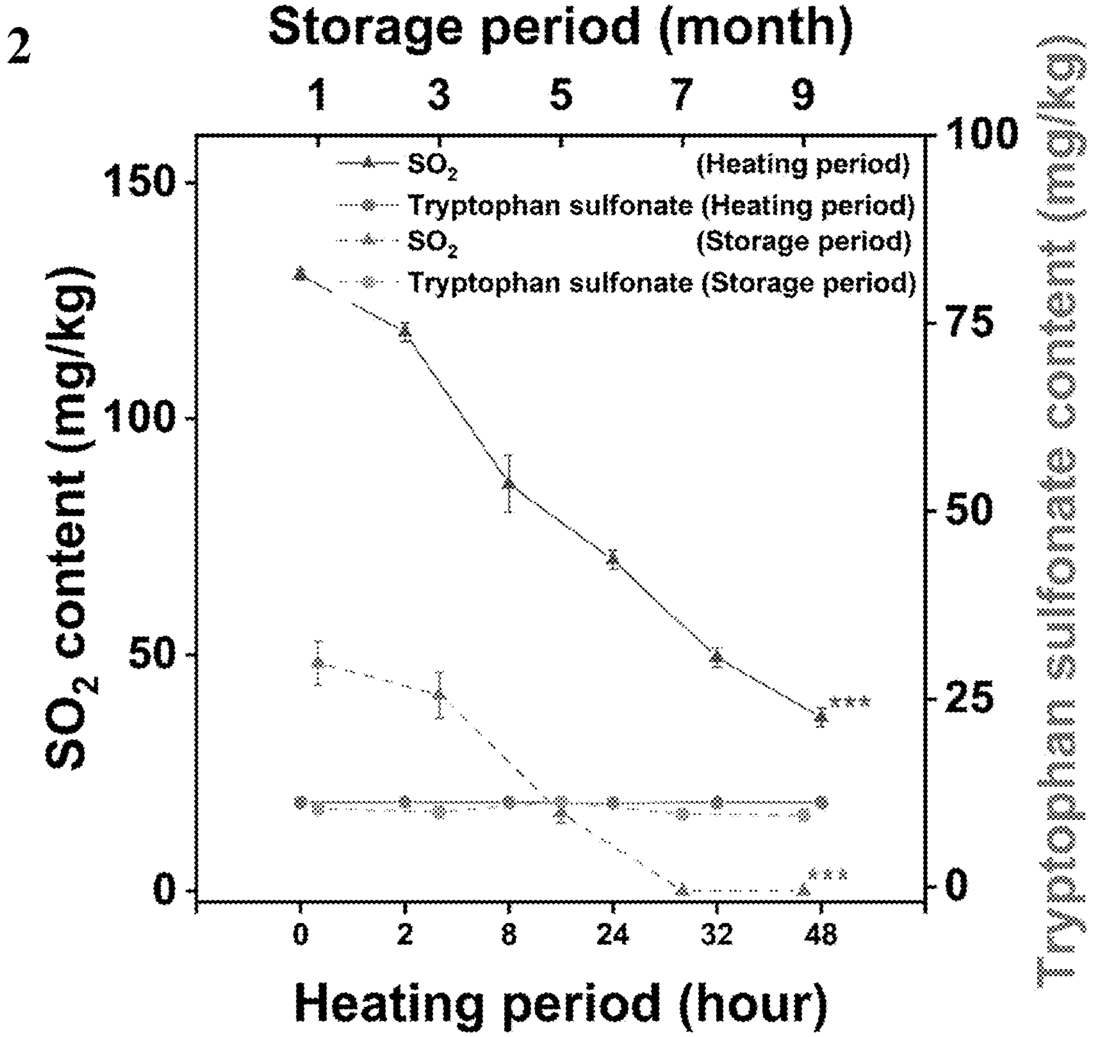
Figure 4:
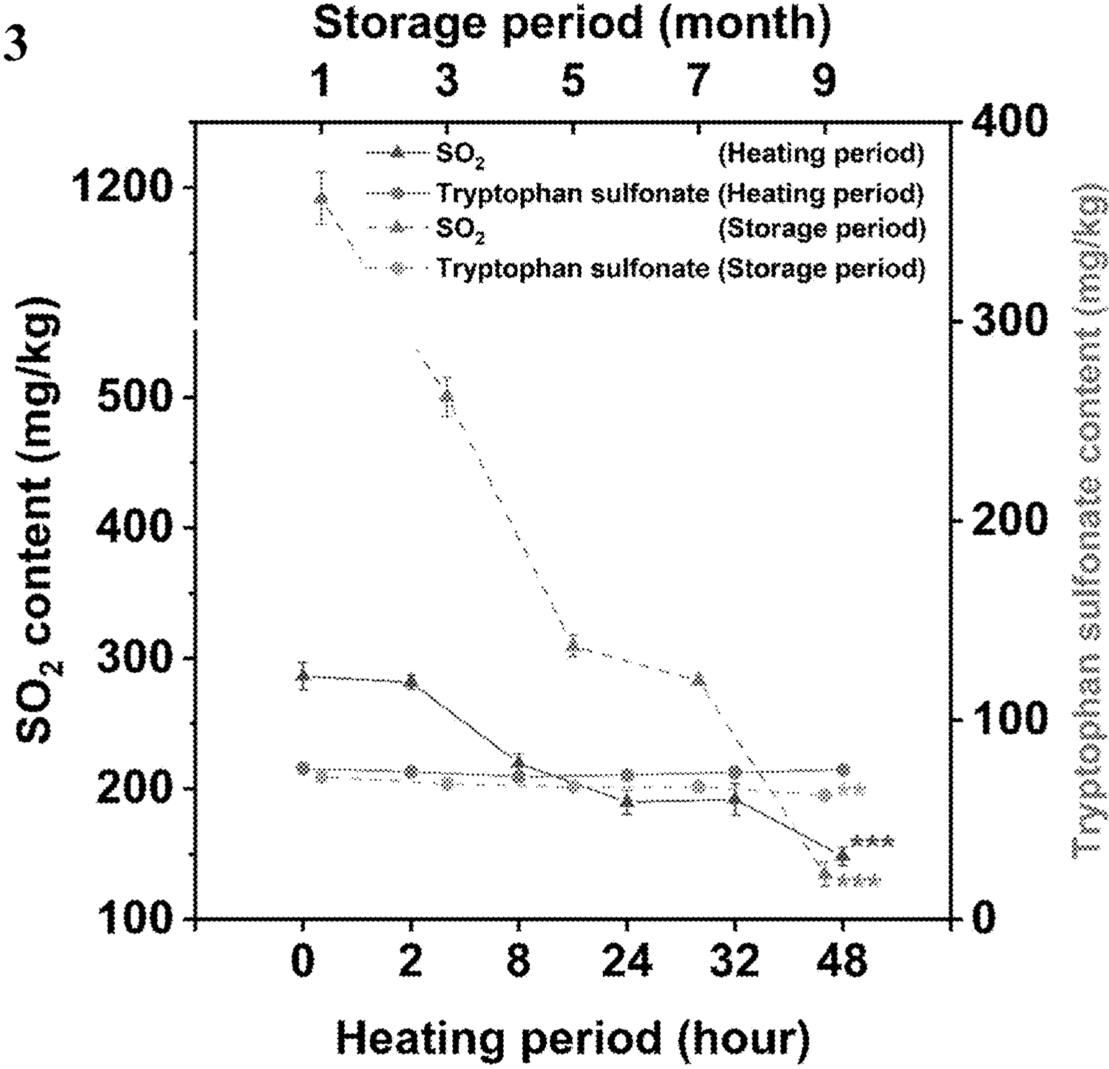
Figure 4:
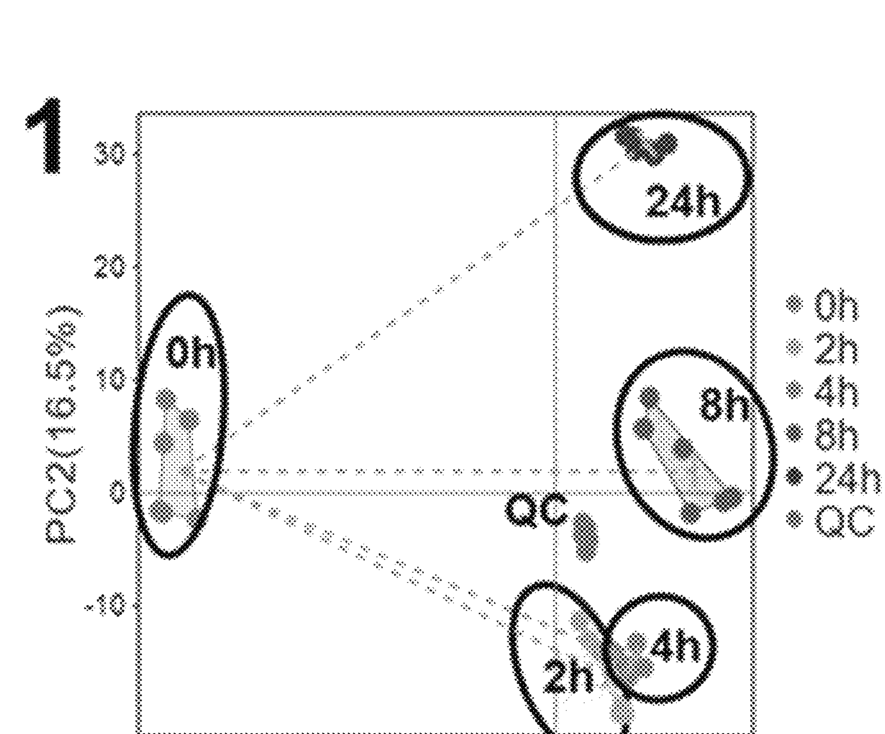
Figure 4:
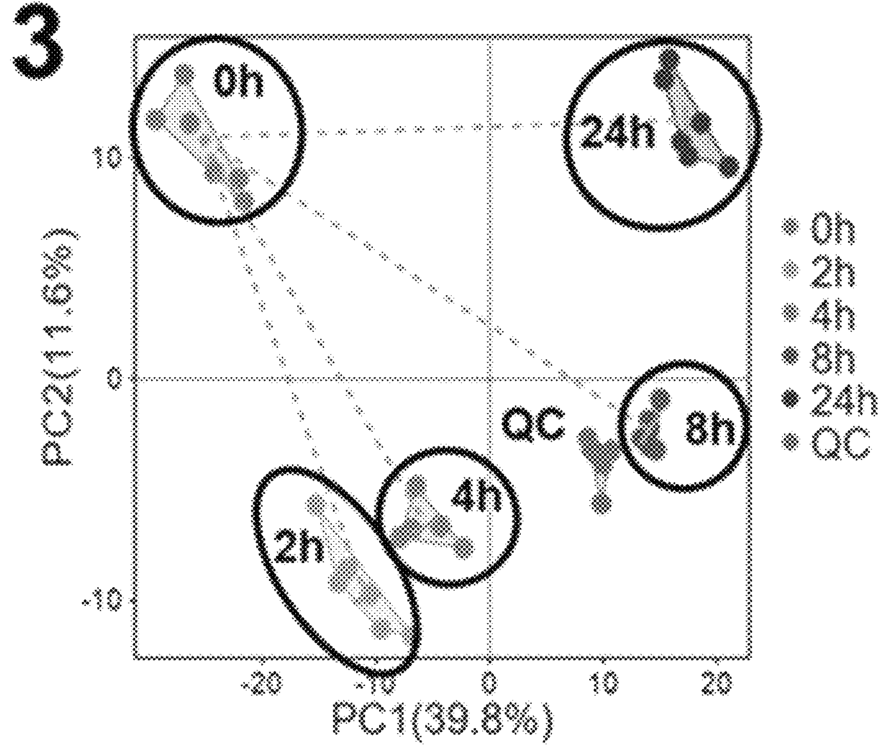
Figure 4:
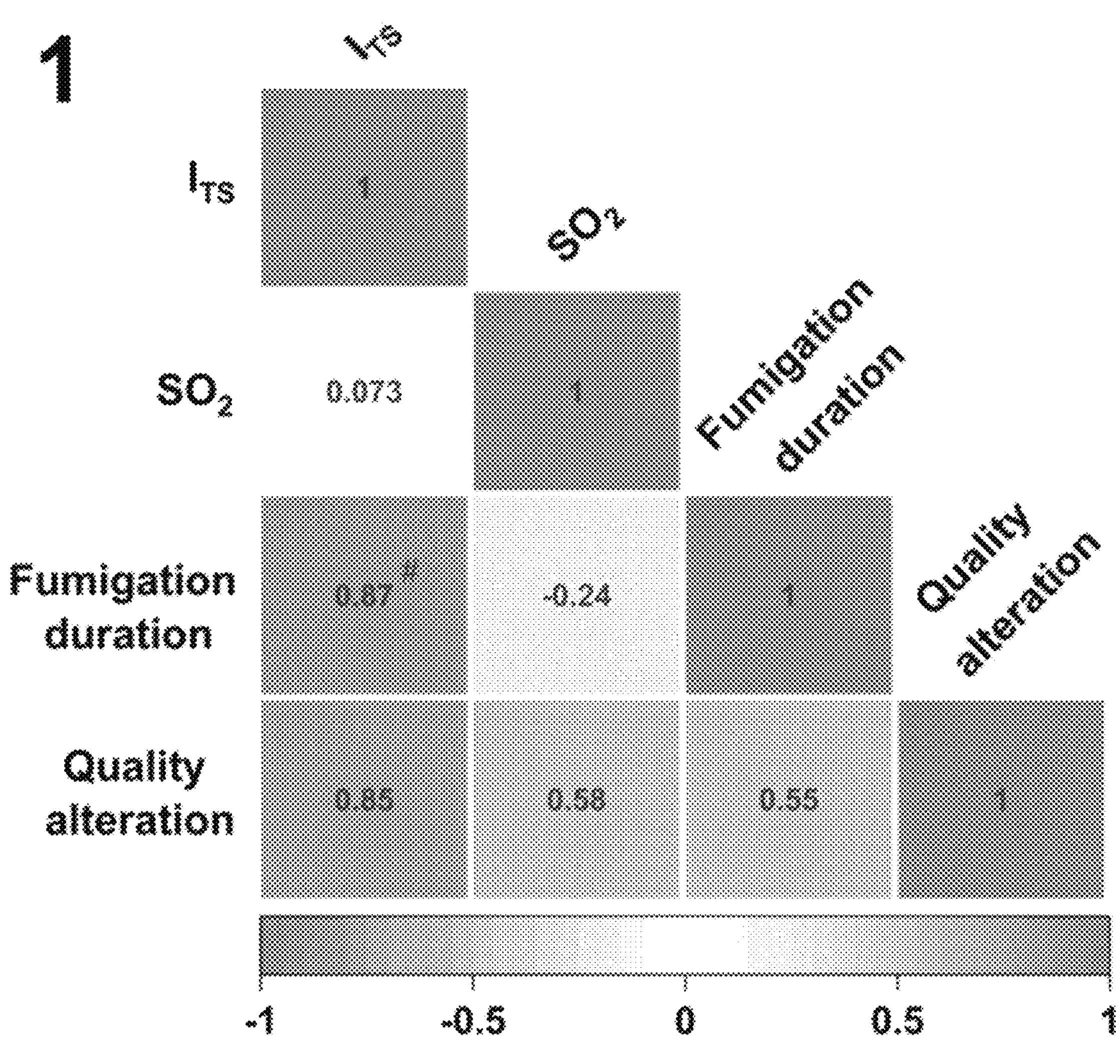
Figure 4:
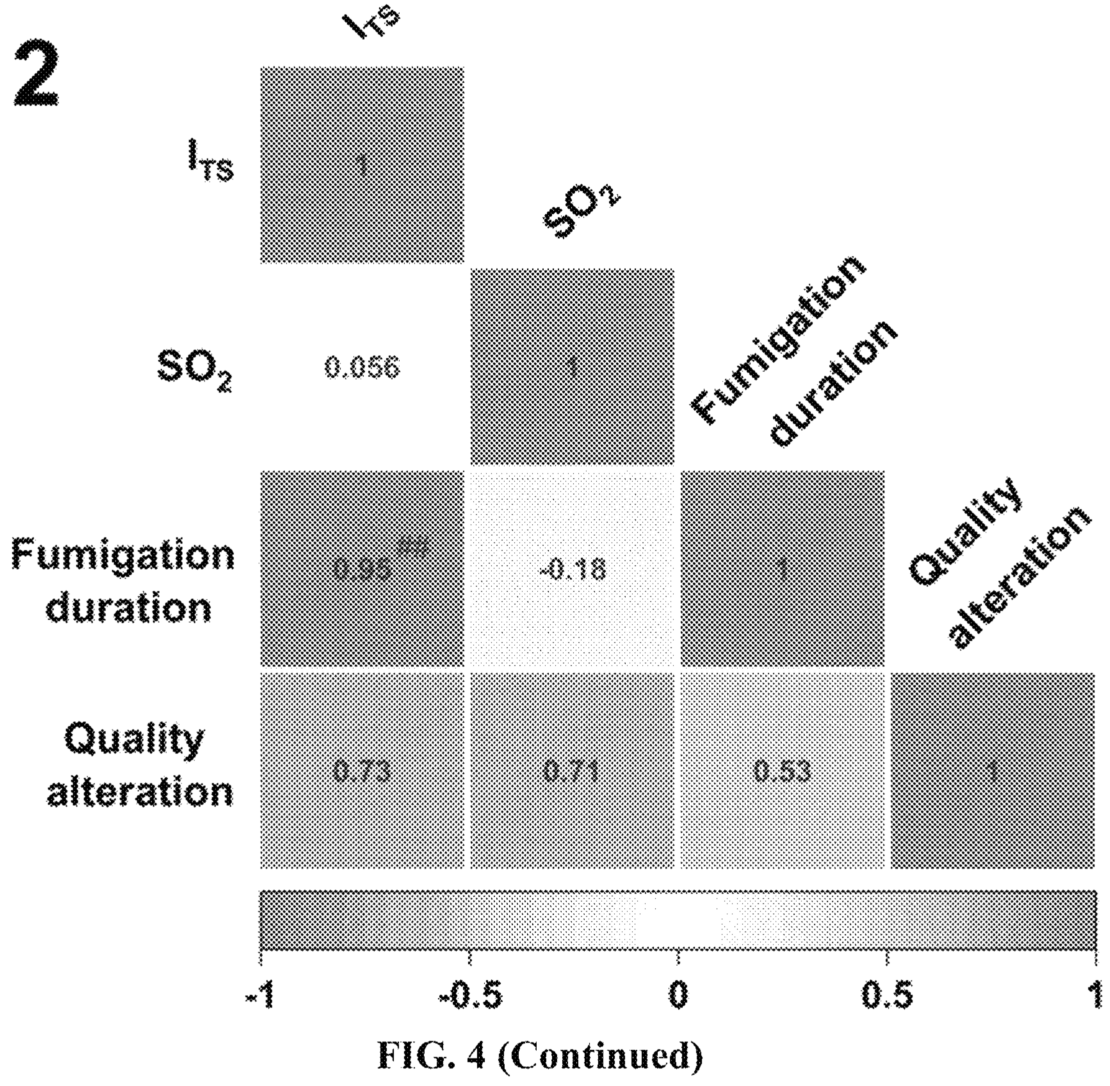
Figure 4:
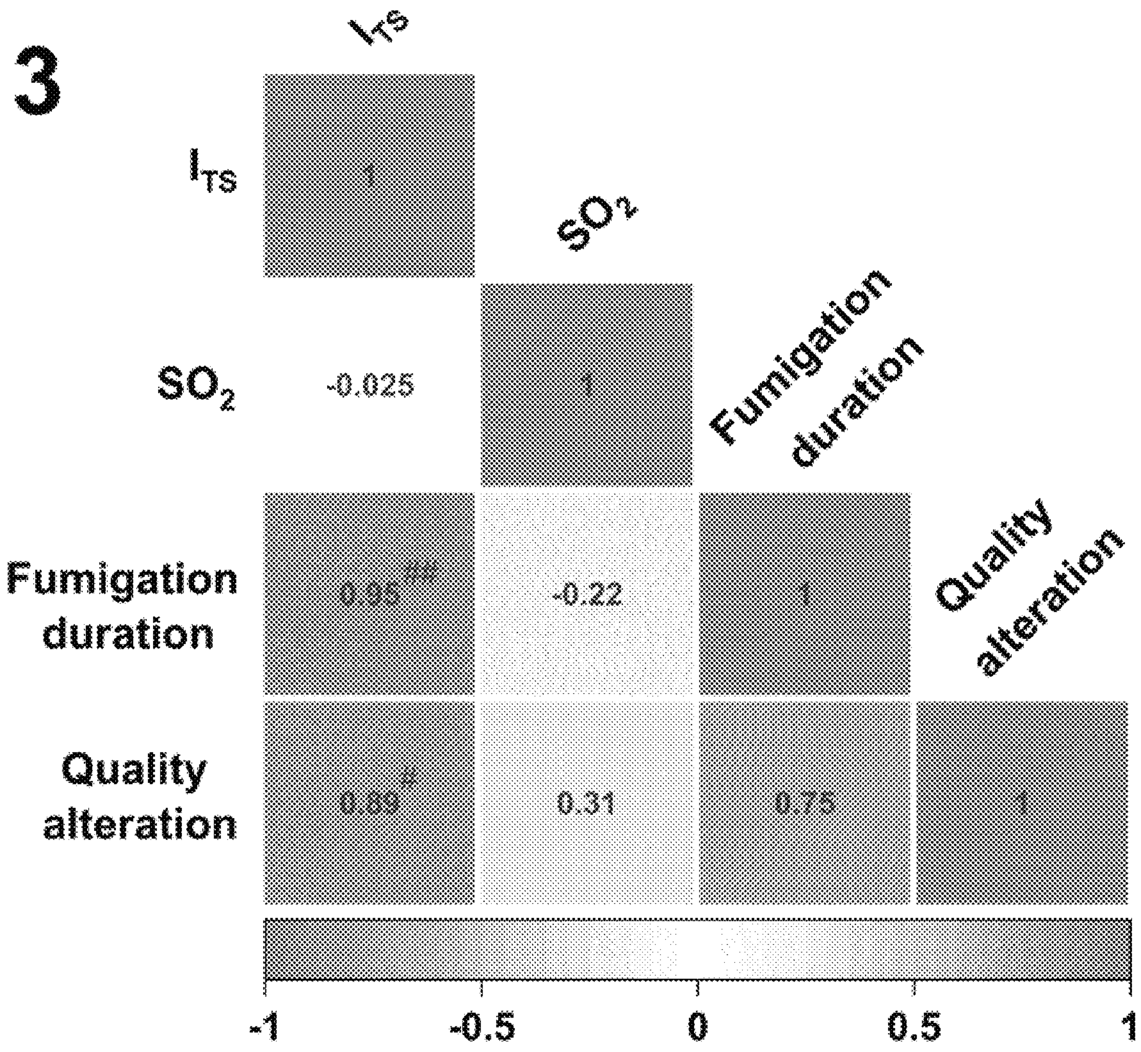
Figure 9:
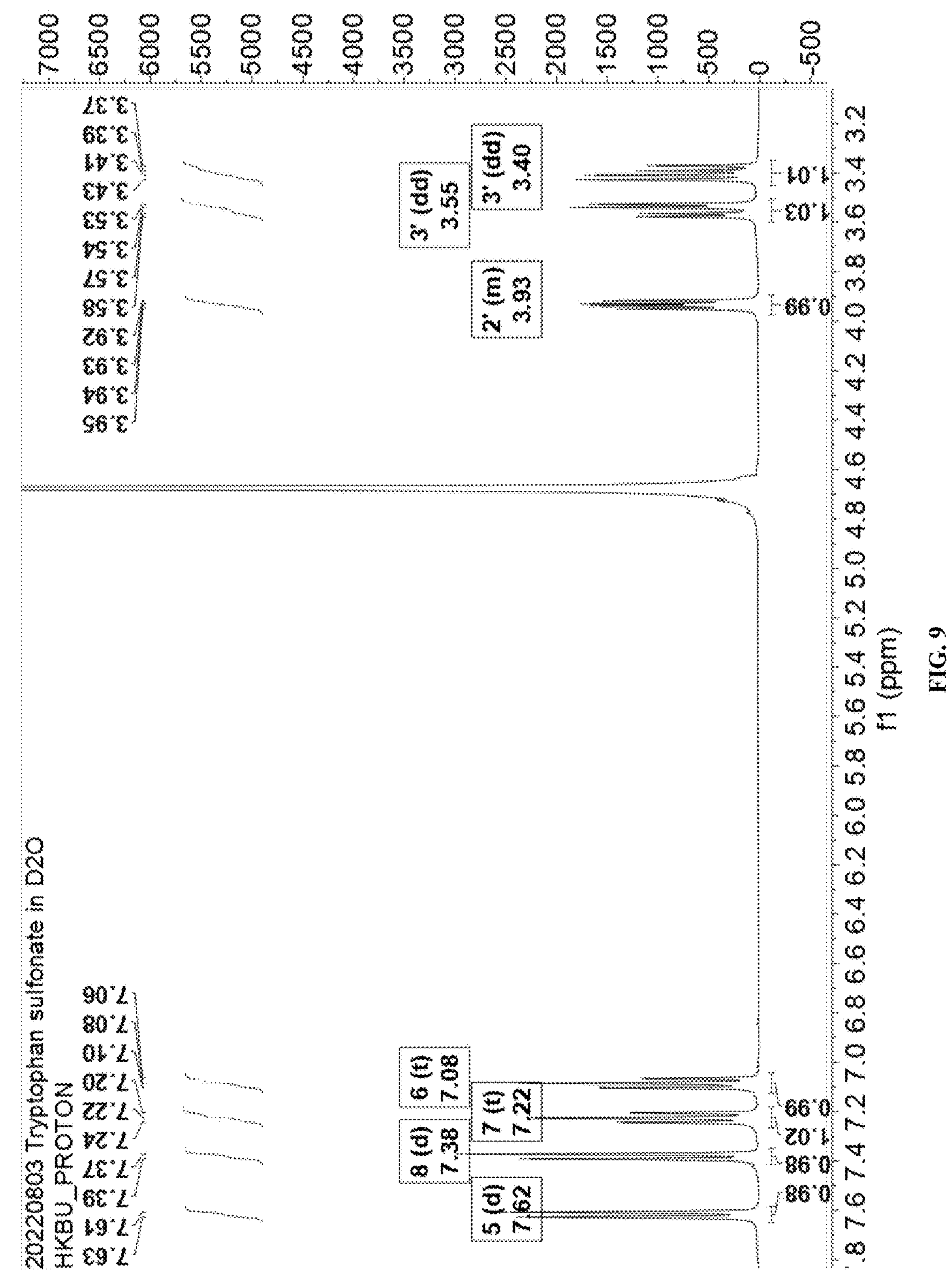
FIG. 9 depicts NMR spectra ($D_2O$) of tryptophan sulfonate. $^1H$ (A), $^{13}C$ (B), HSQC (C), COSY (D), and HMBC (E).
Figure 9:
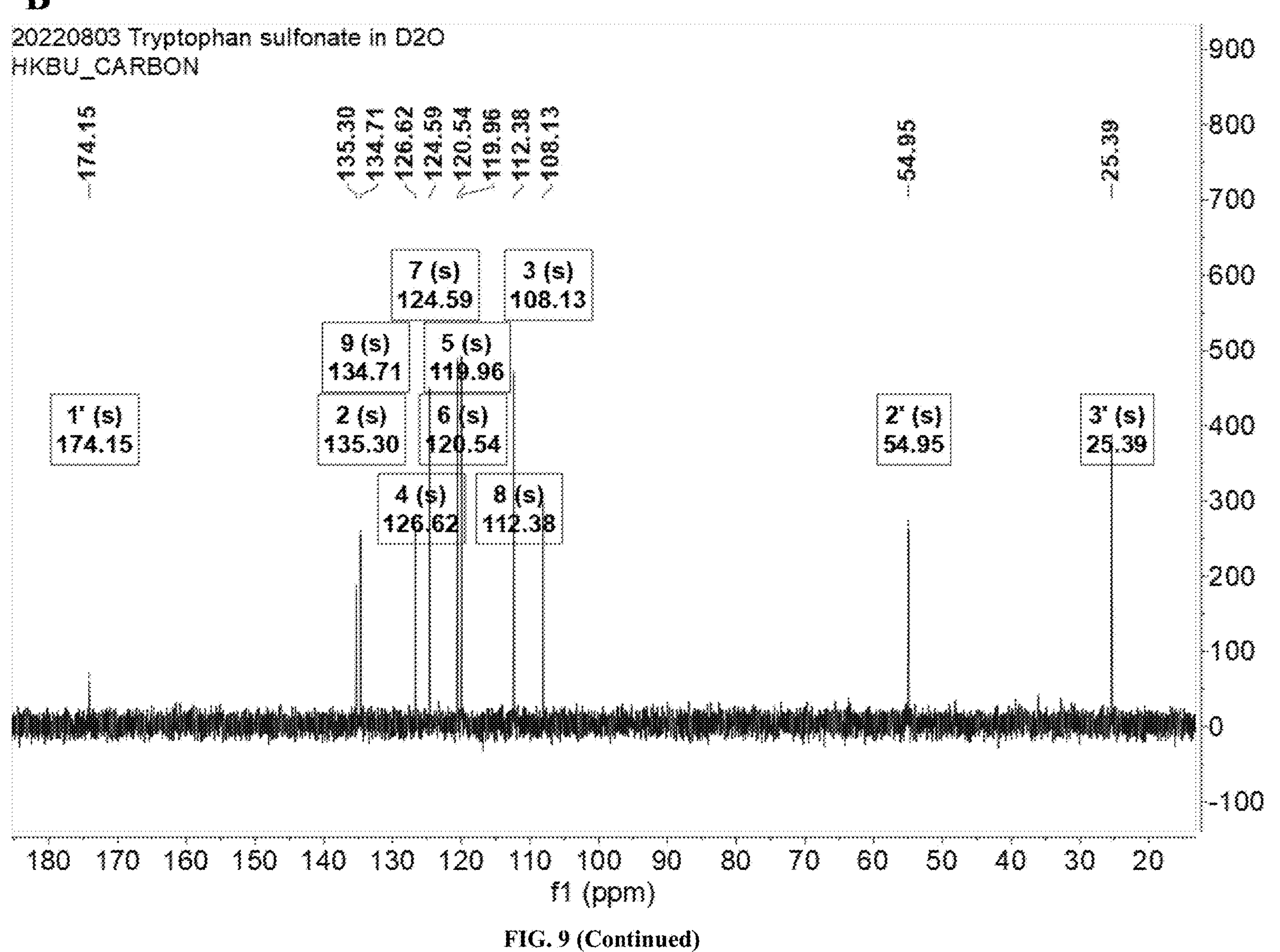
Figure 9:
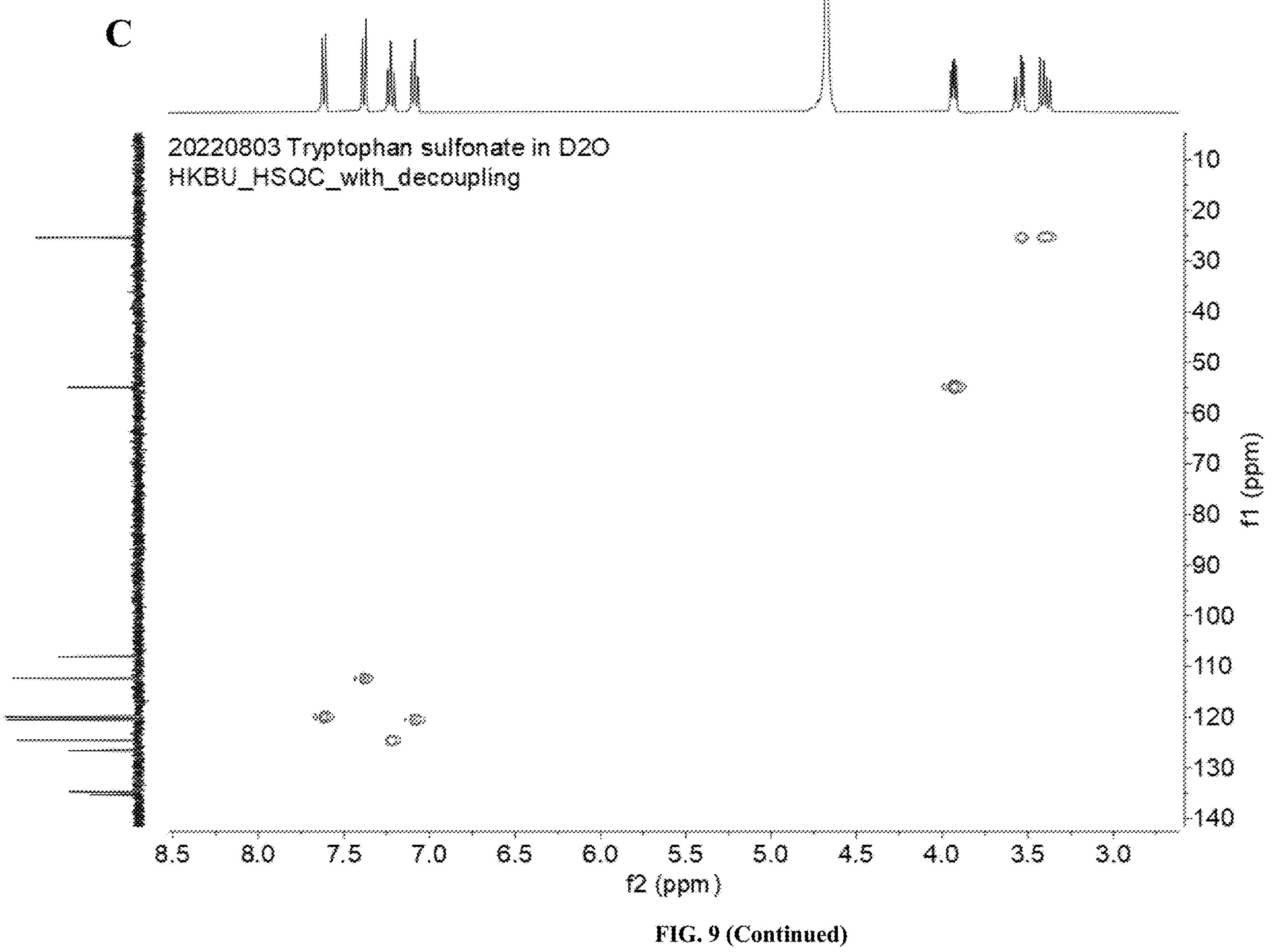
Figure 9:
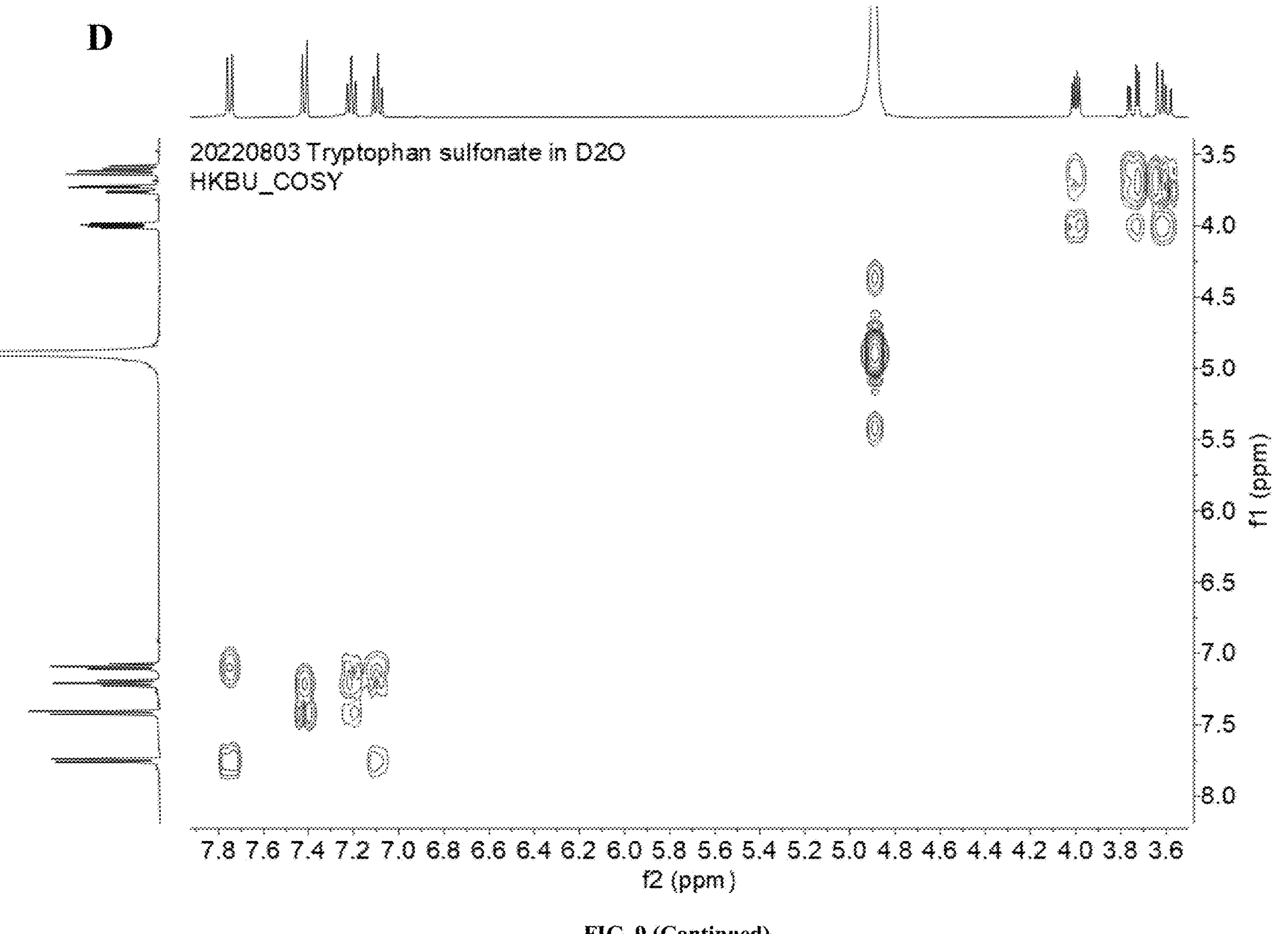
Figure 9:
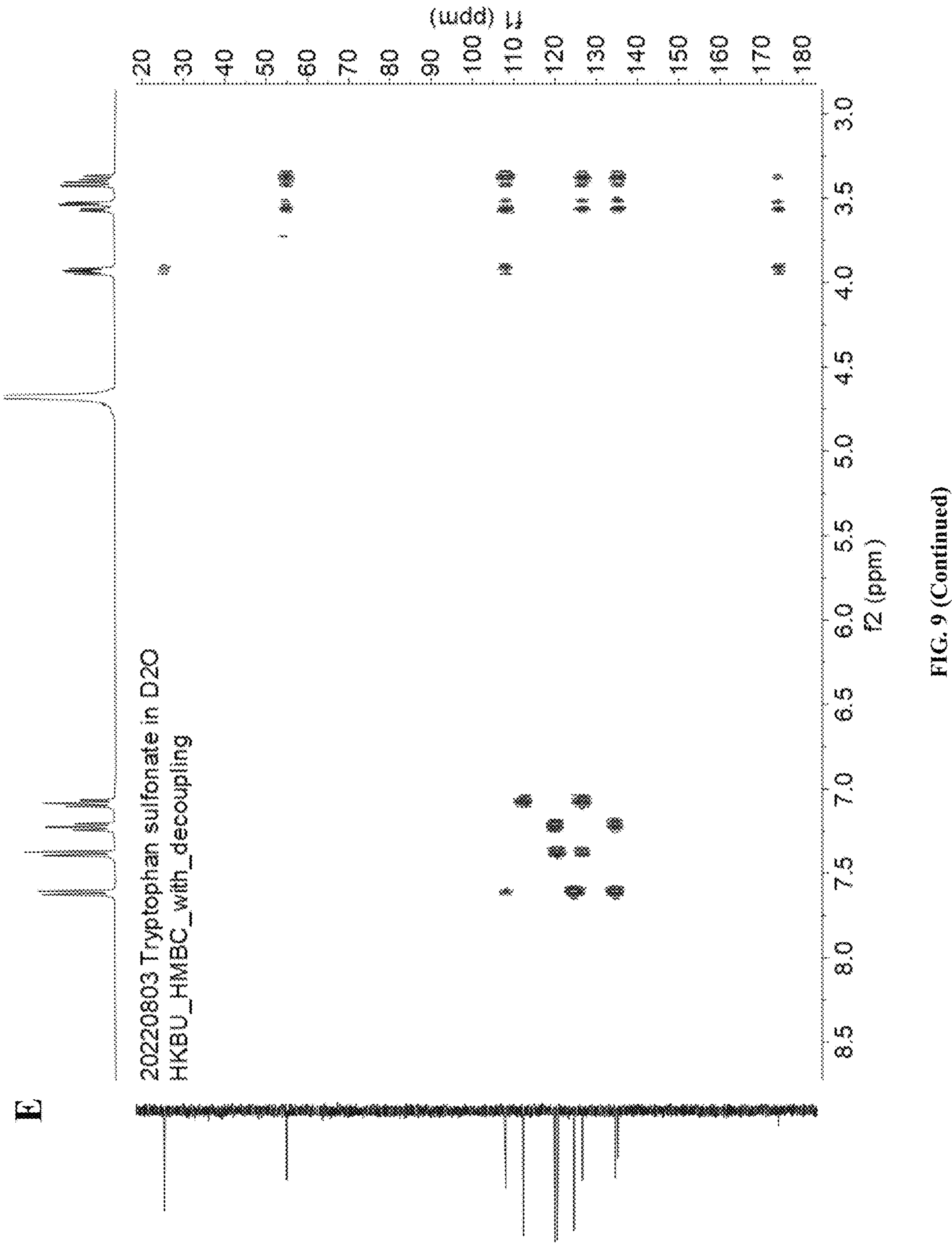
Figure 10:
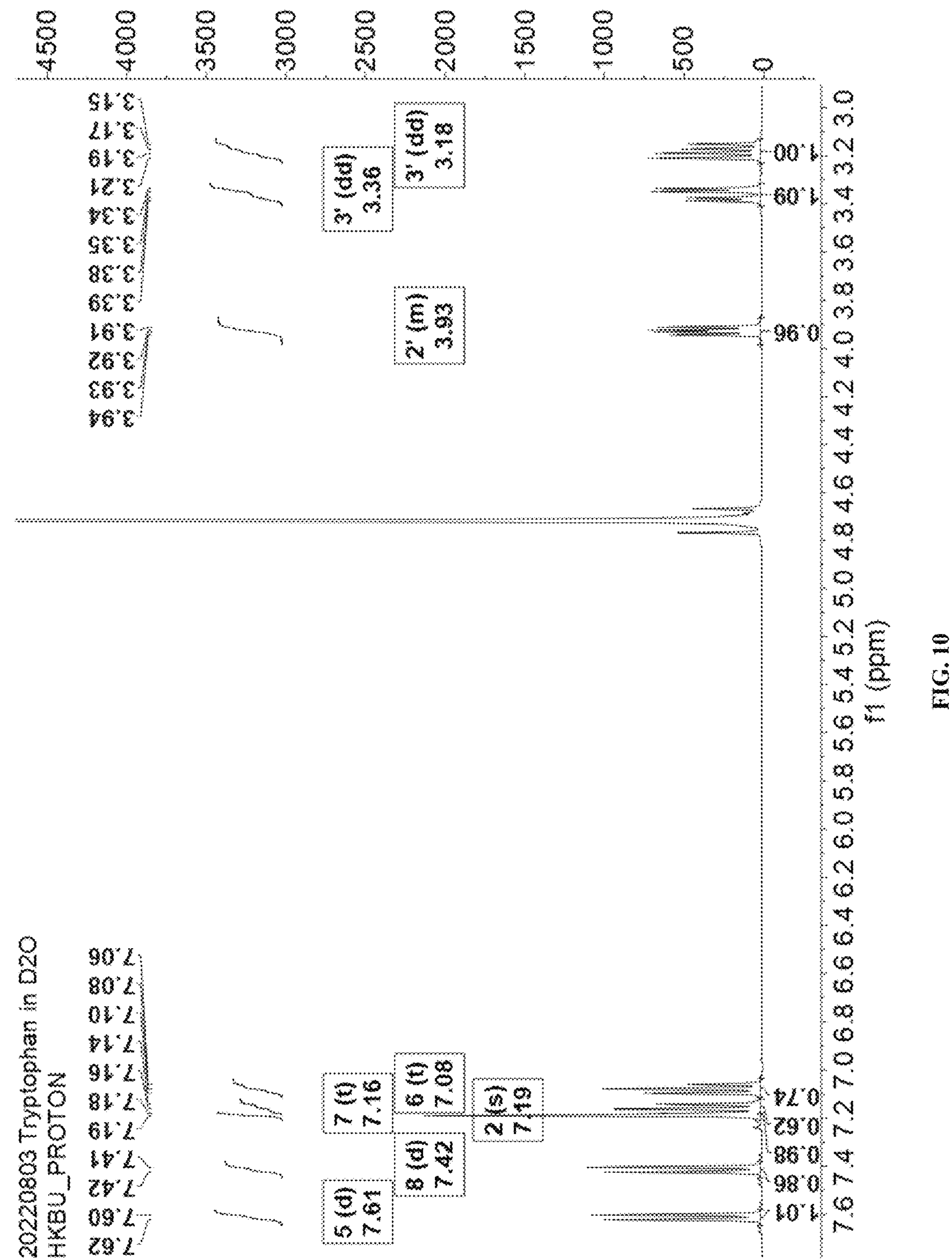
FIG. 10 depicts NMR spectra ($D_2O$) of tryptophan. $^1H$ (A) and $^{13}C$ (B).
Figure 10:
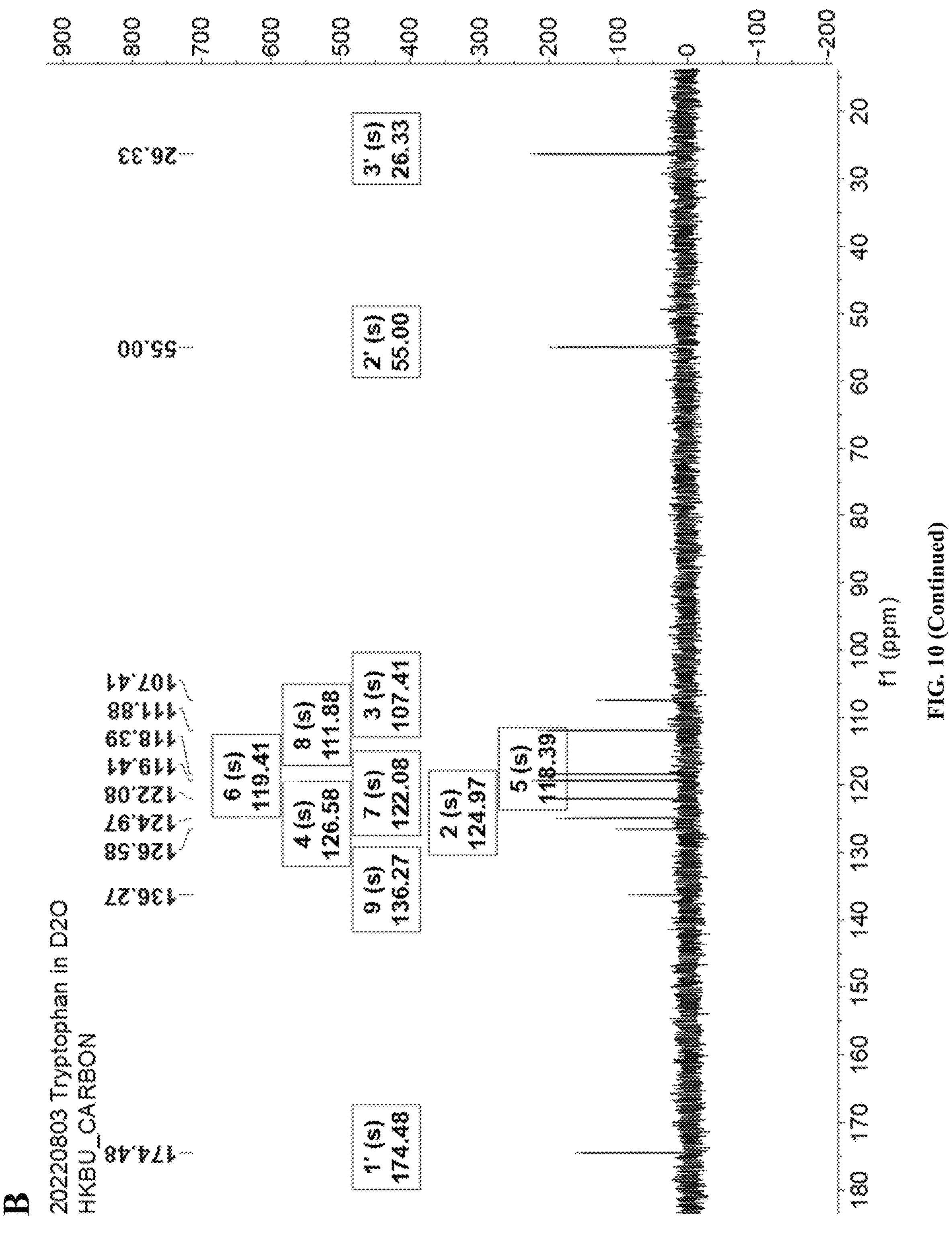

To further explore if and why tryptophan sulfonate is more accurate than sulfites as the chemical marker for the inspection of sulfur-treated products, their generation and variation during sulfur treatment and subsequent storage were then investigated using ginger, yam, and ginseng as case studies. As shown in FIG. 4A, during 24 hs of fumigation, the $SO_2$ content in the three treated samples increased quickly to the peak values ($p<0.01$ for all, vs the $0^{th}$h) in the first 2 h (1297.87 mg/kg in yam) or 4 h (63.78 mg/kg in ginger, 1179.41 mg/kg in ginseng), and then significantly decreased ($p<0.001$ for yam and ginseng, $p<0.05$ for ginger, vs the $2^{nd}$ and 4th h, respectively) till the $24^{th}$ h (23.78 mg/kg in ginger, 372.56 mg/kg in yam, 311.02 mg/kg in ginseng). As to tryptophan sulfonate, it was already detected in all the samples even by 2 h fumigation. Afterwards, in contrast to the content fluctuation of $SO_2$, tryptophan sulfonate gradually increased over the 24 hs of fumigation (+240.26 mg/kg in ginger, +70.44 mg/kg in yam, +168.37 mg/kg in ginseng; $p<0.001$ for all, vs the $0^{th}$ h), meanwhile tryptophan accordingly decreased (−111.63 mg/kg in ginger, −148.40 mg/kg in yam, −704.79 mg/kg in ginseng; $p<0.001$ for all, vs the $0^{th}$ h). We learned that manufacturers and wholesalers often further process sulfur-treated products by heating or by extending the storage time to reduce residual sulfites and thereby meet regulatory standards (Xu et al., 2020). Therefore, stability tests involving short-term heating and long-term storage were performed. Samples were heated continuously for 48 hs, and $SO_2$ and tryptophan sulfonate in the three samples were measured at different times. As shown in FIG. 4B, $SO_2$ constantly diminished in the sulfur-fumigated ginger, yam, and ginseng ($p<0.001$ for all, vs the $0^{th}$ h) by 62.90%, 71.83%, and 48.19%, respectively, while the contents of tryptophan sulfonate were more reliable, slightly varying from 17.12-17.50 mg/kg (+2.22%) for ginger, 11.62-11.20 mg/kg (−3.60%) for yam, and 75.67-75.10 mg/kg (−0.75%) for ginseng (no significant difference for all, vs the $0^{th}$ h). During long-term storage for 9 months, $SO_2$ and tryptophan sulfonate in the three samples were tested every 2 months. Surprisingly, as shown in FIG. 4B, $SO_2$ sharply declined in the sulfur-fumigated ginger, yam, and ginseng by 91.23%, 100%, 88.72%, respectively ($p<0.01$ for all, vs the $1^{st}$ month). In the case of yam, $SO_2$ was not even detected after 7 months of storage. By contrast, the contents of tryptophan sulfonate in the samples were much more stable, ranging from 21.11-19.72 mg/kg (−6.58%) for ginger, 10.37-9.54 mg/kg (−8.04%) for yam, and 71.52-62.34 mg/kg (−12.85%) for ginseng after the 9 months of storage ($p<0.01$ for ginseng, while there was no significant difference for the others, compared with the $1^{st}$ month).

The initial sulfur fumigation could cause the accumulation of free and reversibly bound sulfites, thereby resulting in the increase of detected $SO_2$ in the first 2 or 4 hs. However, the decrease of $SO_2$ thereafter could be because the free and reversibly bound sulfites that accumulate during the early stages of fumigation readily interact with original components of the product and transform them into sulfur-containing derivatives, as we previously revealed in the case studies of ginger (Wu et al., 2018), yam (Chan et. al., 2023), and ginseng (Li et al., 2012). The results clearly revealed that the content of $SO_2$ did not consistently change during the sulfur fumigation. The test of the stored sulfur-fumigated samples showed that residual sulfites were unstable even after the sulfur treatment, which further impaired the power of sulfite assay in the inspection of sulfur-treated products. For example, as aforementioned the false-negative result was obtained by the sulfite assay for the sulfur-fumigated yam after 7-month storage. Compared to $SO_2$, tryptophan sulfonate showed a liner increase trend by the sulfur fumigation and higher stability during the storage. The detection of tryptophan into sulfonated derivative was sensitive to the sulfur treatment conditions. After that, the consistent increase with fumigation duration and the high stability during the following 9 months of storage and 48 hours of heating means tryptophan sulfonate is a durable chemical marker for sulfur-treated products even after long-term storage or heating. All the attributes of tryptophan sulfonate have demonstrated that it could be a better chemical marker than residual sulfites for accurately determining if a product has been treated with sulfur.

Correlation with Sulfur Treatment Duration and Quality Variation

We have found that the $SO_2$ content did not consistently change with the increase of fumigation duration, i.e., more $SO_2$ did not indicate longer fumigation duration, and vice versa. The fact suggested that $SO_2$ content does not represent the duration of sulfur treatment. In contrast, the consistent increase of tryptophan sulfonate with fumigation duration supported that tryptophan sulfonate has the potential to accurately indicate the duration of sulfur treatment. To confirm this, the correlations between the fumigation duration and $SO_2$ or tryptophan sulfonate were further investigated. Considering that the level of tryptophan sulfonate is affected by not only the sulfur treatment extent but also the original amount of tryptophan in the product, we propose a new index $I_{TS}$, calculated by the following equation (Eq. 3), in which $C_{TS}$ and $C_T$ denote the concentrations of tryptophan sulfonate and tryptophan, respectively.

$$I_{TS}(\%) = \frac{C_{TS}}{C_{TS} + C_T} \times 100\% \quad \sim \text{Eq. 3}$$

As shown in FIG. 4A, $I_{TS}$ significantly increases as fumigation duration is prolonged. The correlation analysis (FIG. 4D) reveals significant positive correlation between $I_{TS}$ and the fumigation duration ($p<0.01$ in ginger and ginseng, $p<0.05$ in yam), and no correlation between $SO_2$ content and fumigation duration in all the samples. The strong positive correlation between the fumigation duration and $I_{TS}$ suggests higher accuracy of the proposed $I_{TS}$ value than $SO_2$ content to indicate the duration of sulfur treatment. In addition, for a long time, people have been concerned only about the damage from ingesting xenobiotics (e.g., sulfites) generated by sulfur treatment, but have largely ignored the deleterious impact on the inherent quality of the treated products. As a result, residual sulfites have been well accepted as a chemical marker for quality evaluation of sulfur-treated products; the higher levels of sulfites imply a lower quality of the product. However, given the high instability of sulfites, we suspected the correlation between the sulfite contents and the quality of treated products. Therefore, we characterized the quality of all the samples of ginger, yam, and ginseng tested in the 24 h sulfur fumigation by the untargeted metabolomics and then investigated the correlation between the $SO_2$ content and the quality variation. The score plots by PCA showed that, in each case study of ginger, yam, and ginseng, the sulfur-fumigated samples were located away from the non-fumigated samples (0 h), and the sulfur-fumigated samples with longer fumigation progressively shifted away from the non-fumigated samples (FIG. 4C). The result indicates that sulfur fumigation significantly lowers the quality of fumigated samples, and longer fumigation causes commensurately greater effects. However, correlation analysis (FIG. 4D) found that the $SO_2$ content showed no significant correlation with the sample quality variation, providing further evidence that residual sulfite is insufficient as a chemical marker to represent the quality of sulfur-treated products. In contrast, quality variation and $I_{TS}$ in the case of ginseng showed significant correlation ($p<0.05$). For the other two cases, $I_{TS}$ also showed more correlation with quality alteration than $SO_2$ content ($p=0.161$ vs $p=0.177$ in ginger; $p=0.071$ vs $p=0.304$ in yam). The result suggests the potential of tryptophan sulfonate as a new chemical marker for quality control of sulfur-treated products. Moreover, tryptophan, as an essential amino acid, has been shown to have a significant impact on human health. Upon oral administration, tryptophan is co-metabolized by both the gut microbiota and the host, resulting in the generation of numerous metabolites. Some of these metabolites, such as serotonin and melatonin, play diverse physiological functions in the body, such as regulating mood, appetite, sleep, immune function, and blood pressure (Paredes et al., 2009). However, some indole metabolites of tryptophan can lead to toxicity in specific organs, such as the liver and kidneys (Ye et al., 2022). Tryptophan sulfonate, as a newly discovered derivative of tryptophan, shares a similar structure with tryptophan and certainly warrants further investigation, including its in vivo kinetics, bioactivity, and toxicity, which are relevant topics for future research.

Methodological Performance

In addition to the intrinsic nature of a chemical marker, the experimental procedures are also decisive for assay accuracy. As aforementioned, sample preparation and testing procedures involved in the sulfite assay are complicated, further affecting the qualitative and quantitative results. For example, in titration, the subjective judgement of the endpoint from human eyes and the limited pH range of certain indicators can result in inconsistency of results and a large relative standard deviation among samples (Zhong et al., 2012). With the MS method developed for sulfite determination, precolumn derivatization and purification are normally required due to the highly unstable form of sulfites. This represents opportunity for systematic and accidental errors, as evidenced by a case study in which large relative standard deviations were shown (Carlos and de Jager, 2017). Furthermore, the complicated operations are laborious and time-consuming, impeding the application of these methods in high-throughput inspection, which is desired for the screening of large sample amounts of commercial sulfur-treated products.

Here we compared the performance of the tryptophan sulfonate assay with that of the sulfite assay. As summarized in Table 4, the tryptophan sulfonate assay is more sensitive (LOQ=0.002 mg/kg), precise (RSD≤3.3%), and accurate (104.8-108.2%), compared to the sulfite assay in which the LOQ was 10.00 mg/kg, precision was >6% in RSD, and recovery was 82.85-88.55%. We also demonstrated that the tryptophan sulfonate assay performs better than the current MS method for sulfur-treated food (linearity (R≤0.990), LOQ (0.12-0.75 mg/kg), precision (RSD<16%), and percent recovery (80-115%) are presented as references) (Carlos et al., 2020; Genualdi and DeJager, 2021; Robbins et al., 2015). In addition, the tryptophan sulfonate assay is stable (RSD≤4.5%) and rapid, involving direct ultrasonic extraction for 1 hour and LC-MS analysis for 2 minutes; simple, only those two procedures; and highly automatic, thereby allowing parallel handling of batches of samples. In contrast, the acid-base titration method for determining sulfites requires 2 hours of manual operations including reflux extraction and titration for one sample test. Besides, the tryptophan sulfonate assay involved a more environmental-friendly process than sulfite assay since less sample amount and organic solvents were required, i.e., 0.1 g of sample, 10 mL of 70% methanol and 0.04 mL of acetonitrile in extraction and chromatographic separation were used per sample test. In contrast, the acid-base titration for determining sulfites required 10.0 g of sample, 10 mL of 6 M hydrochloric acid, 50 mL of 3% hydrogen peroxide, and certain amounts of methyl red indicator and 0.01 M sodium hydroxide titrant depending on the sulfite content in the sample. Even 50 g of sample amount and different reagents (e.g., 0.2% formaldehyde, chloroacetic acid, isotope sodium sulfite, ammonium acetate and acetonitrile) for extraction and precolumn derivatization were needed in current MS analysis for the sulfite assay (Robbins et al., 2015). In summary, the newly developed tryptophan sulfonate assay is more accurate and efficient than the sulfite assay for the inspection of sulfur-treated products.

Conclusion

In this study, we identified tryptophan sulfonate as a chemical marker of sulfur-treated food products by UPLC-QTOF-MS/MS-based untargeted metabolomics and then elucidated its chemical identity by chromatographic separation, NMR analysis and chemical synthesis. Next, a tryptophan sulfonate assay was developed by UPLC-QqQ-MS/MS to demonstrate its applicability for the inspection of sulfur-treated products. 50 commercial food samples were tested, in which tryptophan sulfonate showed a higher specificity to sulfur-treated products than sulfites. The stability testing indicated that tryptophan sulfonate is more stable than sulfites if a product is heated after sulfur treatment, or during long-term storage. Moreover, the duration of sulfur treatment was found to strongly correlate with the index of tryptophan sulfonate ($I_{TS}$) but not the content of sulfites. Methodological comparison further revealed that, compared to the sulfite assay, the tryptophan sulfonate assay produced more robust validation data and it was easier to perform, faster, more automated, and more environmental-friendly. The major limitation of this study is that the assay relied on the presence of tryptophan in food as a prerequisite, which makes it unable to cover all food products, particularly those that rarely contain tryptophan. Hence, it is imperative to expand the sample pool for further investigation to confirm the applicability and coverage range of the assay. Nonetheless, based on this prerequisite, all of the results demonstrated that the tryptophan sulfonate assay performed better than the sulfite assay in terms of both accuracy and efficiency. It could serve as a practical approach for the inspection of sulfur-treated products, especially for high-throughput screening of large sample sizes.

EXAMPLES

Material and Methods

Chemical, Reagent, and Materials

Sulfur was purchased from Sigma-Aldrich (Steinheim, Germany). L-Tryptophan, 99%, and sodium bisulfite ($NaHSO_3$) were acquired from Macklin (Shanghai, China). Sodium metabisulfite ($Na_2S_2O_5$) was obtained from Dieckmann (Shenzhen, China). Deuterium oxide ($D_2O$) was obtained from Aladdin (Shanghai, China).

Fresh ginger and yam samples were collected from Fanling, Hong Kong. Fresh ginseng sample was collected from Jilin province, China. 20 additional fresh food samples, including banana, fig, jujube, apricot, guava, peach, pineapple, potato, strawberry, grape, papaya, blueberry, kiwi fruit, longan pulp, mango, starfruit, corn, snow fungus, garlic, and onion were collected from Lokfu, Hong Kong. 50 commercial food samples were purchased in Hong Kong SAR and mainland China, and their detailed information was listed in Table 1 (FIG. 5). The voucher specimens of all samples were deposited at the School of Chinese Medicine, Hong Kong Baptist University, Hong Kong SAR.

Untargeted Metabolomics

Sample Preparation

Sulfur-fumigated and non-fumigated samples of ginger, yam, and ginseng were prepared according to the actual practice of sulfur fumigation by farmers and wholesalers. The collected fresh samples were cut into slices with a thickness of about 0.3 cm. To prepare the sulfur-fumigated samples, 500 g slices were moistened with 10 mL water (1:1, w/v). Sulfur powder (10 g) was heated until it burned, and then the burning sulfur and the wetted slices were carefully put into the lower and upper layers of a desiccator, respectively. Thereafter the desiccator was sealed for 12 h. After the sulfur fumigation, the slices were dried in an oven at 40° C. for 10 h to generate the sulfur-fumigated sample. The non-fumigated sample was prepared by direct drying in an oven at 40° C. for 10 h without sulfur fumigation. Both sulfur-fumigated and non-fumigated samples for each species were prepared with six replicates.

Powders (140 mesh) of each prepared sample were accurately weighed (0.20 g for ginger, 1.00 g for yam, and 0.20 g for ginseng) and then ultrasonicated with 10 mL of 70% methanol for 1 h. The supernatant was obtained after centrifugation (4000 rpm, 10 min) and was filtered by a 0.22 μm PTFE syringe filter for UPLC-QTOF-MS/MS analysis.

UPLC-QTOF-MS/MS Analysis

Untargeted metabolomics analysis was performed by an Agilent 1290 UPLC system coupled with a binary solvent delivery system G4220A, a thermostatic column compartment G1316C, auto-sampler G4226A, and G6540A QTOF mass spectrometer equipped with dual electrospray ionization (ESI) source. The mobile phase consisted of water with 0.1% formic acid (FA) (A) and acetonitrile with 0.1% FA (B). The injection volume was 2 μL, and the column temperature was maintained at 40° C. Quality control (QC) sample was prepared by mixing the equivalent volume from each of the tested samples to observe the system stability and attenuate any analytical variation resulting from system instability.

For ginger, the chromatographic separation was achieved by a Waters ACQUITY BEH C18 column (2.1×100 mm, i.d. 1.7 μm). The UPLC elution conditions were set as follows: isocratic 5% B (0-2 min), 5% to 10% B (2-4 min), 10% to 65% B (4-10 min), 65% to 95% B (10-16 min). The flow rate was 0.4 mL/min.

For yam, the chromatographic separation was achieved by a Waters ACQUITY BEH C18 column (2.1×100 mm, i.d. 1.7 μm). The UPLC elution conditions were set as follows: 15% to 30% B (0-2 min), 30% to 34% B (2-5 min), 34% to 36% B (5-12 min), 36% to 60% B (12-16 min), 60% to 60% B (16-24 min), 60% to 100% B (24-26 min). The flow rate was 0.4 mL/min.

For ginseng, the chromatographic separation was achieved by a Waters ACQUITY HSS T3 column (2.1×100 mm, i.d. 1.8 μm). The UPLC elution conditions were set as follows: 5% to 15% B (0-1 min), 15% to 35% B (1-10 min), 35% to 42% B (10-15 min), 42% to 80% B (15-18 min), 80% to 95% B (18-19 min). The flow rate was 0.35 mL/min.

The mass spectrometric analysis was performed in negative ion mode, and the parameters in Auto MS/MS full-scan mode were set as follows: nebulizing and JetStream gas flow, 7 L/min; nebulizing and sheath gas temperature, 300° C.; nebulizer pressure, 40 psi; capillary voltage, 3500 V; skimmer, 65 V; fragmentor voltage, 130 V; All peaks in the range of 100-1700 m/z were recorded in the mass spectrum. Collision energies were 25 to 35 V for fragmentation information.

Multivariate Statistical Analysis

The UPLC-QTOF-MS/MS raw data of both sulfur-fumigated and non-fumigated samples were analyzed using MassHunter Qualitative Analysis software (version B.06.00). For data collection, the method parameters were customized as follows: retention time range, 0-10 min; mass range, 100-1000 Da; retention time tolerance, 0.1 min; mass tolerance, 15.0 ppm; peak width at 5% height, 1.0 s; peak-to-peak baseline noise, 0.0; noise elimination level, 6.0; No specific mass or adduct was excluded.

For PCA, the collected data were exported as a comma-separated value file (CSV) and then further processed by MetaboAnalyst 5.0 (Sainte-Anne-de-Bellevue, Quebec, Canada). A list of the peak intensities was generated with the 0.25 m/z of mass tolerance and 30.0 s of retention time tolerance by MetaboAnalyst 5.0 using retention time and mass data (m/z) pairs as the identifier of each peak for the following analysis. Features with multiple missing values and high relative standard deviation (RSD, %) were deleted by selecting the function of removing features with >50% missing values and >10%, respectively. PCA plots were conducted using OmicShare tool (www.omicsshare.com/tools) based on R language. The samples according to type (non-fumigated or sulfur-fumigated) or duration of fumigation (0, 2, 4, 8, or 24 h) were grouped. The confidence level of parameters and the significance level for Hotelling's T2 were set as 95% and 0.05, respectively. Scaled and centered types of coefficients were arranged. $R^2X$ (cum) and $Q^2$ (cum) were examined for the variance and predictive accuracy of the model, respectively.

For volcano plot analysis, the collected data were exported in common event format (CEF) and then were analyzed by Mass Profiler Professional 2.0 software (Agilent Technologies, USA). The unidentified type of experiment was selected, and the samples were divided into two groups, non-fumigated and sulfur-fumigated. Filters were set as follows: minimum absolute abundance, 5000 counts; frequency, entities appearing in samples in only one condition were retained; p-value cut-off, 0.05; changes, 3-fold changes. From volcano plots generated based on these parameters, the metabolites with statistical significance were considered to be targets. The targeted information from the volcano plot analysis, i.e., the retention times and exact molecular weights, was recorded in Microsoft Office Excel (Microsoft Corporation, WA, USA). Conditional formatting in Excel was employed to compare the exact molecular weights of the three samples with matching duplicate values. The same molecular weight in three samples was highlighted.

Isolation and Structure Elucidation of the Chemical Marker

A total of 10.0 kg of dry sulfur-fumigated ginger powder was extracted with 5 L of 70% ethanol three times. The extracts were then combined and evaporated at 55° C. on a rotary evaporator until dry. The residue was suspended in water and extracted with petroleum ether, ethyl acetate, and n-butanol in that sequence to remove untargeted compounds and impurities. The remaining water extract was concentrated into a precipitate and subjected to separation.

The precipitate from the isolation was partitioned into 15 fractions by macroporous resin D101 (Macklin, Shanghai, China) eluted with various ratios of ethanol and water solution (0%:100% to 100%:0%, v/v). The target fractions (fractions 2 to 5) were merged and then purified by semi-preparative high-performance liquid chromatography (semi-prep-HPLC), which was performed with an Agilent 1100 system (Agilent Corp., MA, USA), equipped with a binary solvent delivery system G1312A, auto-sampler G1367A, and DAD detector G1315B. The separation was accomplished by YMC-Pack ODS-AQ (250×10.0 mm, i.d. 5 μm) with isocratic elution of acetonitrile:water (2%:98%, v/v) at a flow rate of 4 mL/min, a column temperature of 25° C. and ultraviolet (UV) detection at 220 nm and 275 nm. The final product was subjected to NMR analysis for structural elucidation.

The pure product was dissolved in $D_2O$, and the following spectra were recorded: $^1H$, $^{13}C$, $^1H$-$^1H$ COSY, HSQC, and HMBC on a 400 MHz FT-NMR spectrometer (Bruker Avance-III). Bruker Topspin version 4.1.4 was selected to process and analyze the recorded spectra.

Synthesis of the Chemical Marker

A 200-mL blue-cap bottle containing a solution of L-Tryptophan (1 g) and $NaHSO_3$ (4 g) in water (50 mL) was heated at 120° C. for 30 min using an electrically-heated autoclave (Hirayama Mfg. Corp., Japan). The targeted precipitate was obtained by centrifugation (4000 rpm, 15 min) and then rotary evaporation at 55° C. After that, the precipitate was separated into five fractions by microporous resin D101 eluted with various ratios of ethanol and water solution (0%:100% to 100%:0%, v/v). The target fractions (fractions 1 to 2) were merged and then purified by semi-prep-HPLC using the same separation conditions aforementioned to yield the pure chemical marker.

Quantitative Assay of the Chemical Marker

Sample Preparation

Four batches of ginger, yam, and ginseng were sulfur-fumigated as described above with the fumigation durations of 2, 4, 8, and 24 h. A second set of these four batches were similarly fumigated and used for the stability test. For short-term stability, the sulfur-fumigated samples were heated at 60° C. and sampled at 0, 2, 8, 24, 32, and 48 h. For long-term stability, sulfur-fumigated samples were stored at 25° C. in an air-circulated condition, and then sampled at 1, 3, 5, 7, and 9 months. All the samples were prepared in triplicate and stored at 4° C. for further experiments.

The parallel sets of sulfur-treated and non-treated samples of 20 fresh food samples were prepared using the methods as described herein. Then, the dried powders (140 mesh) of all the self-prepared samples and 50 market samples (0.10 g) were accurately weighed and then ultrasonicated with 10 mL of 70% methanol for 1 h. The supernatant was obtained after centrifugation (4000 rpm, 10 min) and was filtered by a 0.22 μm PTFE syringe filter for UPLC-QqQ-MS/MS analysis.

UPLC-QqQ-MS/MS Analysis

The quantitative assay was performed by an Agilent 1290 UPLC system coupled with a binary solvent delivery system, auto-sampler, and G6460A QqQ mass spectrometer equipped with Jetstream ESI source. The chromatographic separation was achieved by a Waters ACQUITY BEH C18 column (2.1×50 mm, i.d. 1.7 μm). The isocratic elution for 2 minutes was operated with the mobile phase as 5% acetonitrile with 0.1% FA and 95% water with 0.1% FA. The flow rate was 0.4 mL/min. The injection volume was 5 μL and the column temperature was maintained at 40° C.

The mass spectrometric analysis was performed in negative ion mode, and the parameters of the Jetstream ESI source were as follows: drying gas temperature, 300° C.; drying gas flow rate, 8 L/min; nebulizer pressure, 45 psi; capillary voltage, 3500 V. Multiple reaction monitoring (MRM) mode was employed for the analysis, with two ion pairs (m/z 283.14222.0 for tryptophan sulfonate and m/z 203.14116.0 for tryptophan). Agilent Mass Hunter Quantitative Analysis B.06.01 was used for data analysis.

Method Validation

The quantitative assay was validated in terms of linearity, sensitivity, precision, stability, and accuracy. Stock solutions of reference compounds were diluted to six certain concentrations for the construction of calibration curves from plotting the peak areas versus the concentrations of analytes. The limit of detection (LOD) and limit of quantification (LOQ) were determined at S/N (signal to noise) ratios of about 3 and 10, respectively. For the precision test, intra- and inter-day variations were selected in which, for intra-day, the sample was extracted and analyzed in six replicates within one day, whereas for inter-day, the same sample was examined in duplicate for three consecutive days. Variations were expressed by RSD (%) of the data. For the stability test, the sulfur-fumigated sample was extracted and analyzed over periods of 0, 2, 4, 6, 8, 10, 12, and 24 h, and the RSDs of the peak areas of each targeted analytes were taken as the measure of stability. For the accuracy test, the spike recovery was assessed. The sample with known contents of targeted analytes was weighed, and different amounts (high, middle, and low levels) of reference were spiked. Samples were then extracted and analyzed in triplicate. The calculation of spiked recoveries was according to the following equation (Eq. 1):

$$\text{spike recovery (\%)}=(\text{total amount detected}-\text{original amount})/\text{amount spiked}\times 100\%. \quad \text{Eq. 1}$$

Sulfite Assay

Titration

The sulfite assay was performed by acid-base titration (Robbins et al., 2015; AOAC, 2019). Precisely 10 g of sample powder with 400 mL of water and 10 mL of 6 M hydrochloric acid were mixed in a 1000 mL round-bottomed flask. The sample solution was boiled for 1.5 h. A 3% (v/v) hydrogen peroxide solution containing methyl red indicator titrated with 0.01 M sodium hydroxide was used to measure the content of $SO_2$ residues (mg/kg), which was determined by Eq. 2

$$SO_2 \text{ residues (mg/kg)} = \frac{32.03 \times V_B \times C_{NaOH} \times 1000}{W} \quad \sim \text{Eq. 2}$$

where 32.03 is the milliequivalent weight of $SO_2$, VB is the volume (mL) of NaOH required to reach end point, $C_{NaOH}$ is the concentration of NaOH used, and W is the weight (g) of sample added.

Method Validation

The titration method was validated in terms of sensitivity, precision, and accuracy. A stock solution of $Na_2S_2O_5$ indicated as $SO_2$ was diluted in water to obtain an appropriate concentration of standard solution for the following analysis. LOQ was determined at the lowest concentration of $Na_2S_2O_5$ detected with the RSD less than 5% (n=6). For the precision test, intra- and inter-day variations were selected in which, for intra-day, the sample was extracted and analyzed in six replicates within one day, whereas for inter-day, the same sample was examined in duplicate for three consecutive days. For the accuracy test, the recovery test was conducted by spiking sulfite-free samples with three concentrations (100, 750, and 1500 mg/kg) of $Na_2S_2O_5$, then extracted and analyzed in triplicate. Spike recoveries were calculated according to the Eq. 1.

Quantitative Statistical Analysis

All results obtained in the quantitative assays were shown as mean±standard deviation of three determinations. The obtained data were integrated into charts by OriginPro 2021 (OriginLab Corporation, USA) or Prism 8 software (GraphPad, USA) and analyzed with an unpaired t-test where p-value<0.05 is considered significant. Heatmap analysis was performed using OriginPro 2021 (OriginLab Corporation, USA).

What is claimed is:

1. A method of identifying a sulfur-treated food product, the method comprising:

providing a sample comprising a food product;

analyzing the sample using an analytical method to determine whether the sample comprises tryptophan sulfonate; and identifying based on whether the sample comprises tryptophan sulfonate that the food product is sulfur-treated, wherein the presence of tryptophan sulfonate indicates that the food product is sulfur-treated.

2. The method of claim 1, wherein the analytical method comprises gas chromatography, liquid chromatography, thin layer chromatography, mass spectrometry, nuclear magnetic resonance, a stain, ultraviolet light absorption, or a combination thereof.

3. The method of claim 1 further comprising calculating a ratio of tryptophan sulfonate to tryptophan in the sample and determining based on the ratio of tryptophan sulfonate to tryptophan in the sample the intensity of sulfur treatment the food product was subjected to.

4. The method of claim 1, wherein the step of analyzing the sample comprises analyzing the sample using a mass spectroscopy method thereby generating mass spectroscopy data and determining whether the mass spectroscopy data comprises one or more first markers indicative of the presence of tryptophan sulfonate.

5. The method of claim 4, wherein the mass spectrometry method is tandem mass spectroscopy (MS/MS) and further comprises liquid chromatography.

6. The method of claim 4, wherein the mass spectrometry method comprises high-performance liquid chromatography (HPLC-MS/MS) or ultra-performance liquid chromatography (UPLC-MS/MS).

7. The method of claim 4, wherein the one or more first markers comprise an observed mass to charge ratio (m/z) selected from the group consisting of 283.04±0.01, 267.02±0.01, and 222.02±0.01 in negative ion mode or from the group consisting of 285.05±0.01, 146.06±0.01, and 118.06±0.01 in positive ion mode.

8. The method of claim 4, wherein the mass spectroscopy method comprises multiple reaction monitoring (MRM) mode and the one or more first markers comprise an observed mass to charge ratio (m/z) of 283.04±0.01→222.02±0.01.

9. The method of claim 4, wherein the step of analyzing the sample further comprises determining whether the mass spectroscopy data comprises one or second more markers indicative of the presence of tryptophan.

10. The method of claim 9, wherein the one or more second markers comprise an observed mass to charge ratio (m/z) selected from the group consisting of 203.07±0.01 and 116.05±0.01.

11. The method of claim 9 further comprising calculating a ratio of tryptophan sulfonate to tryptophan in the sample and determining based on the ratio of tryptophan sulfonate to tryptophan in the sample the intensity of sulfur treatment the food product was subjected to.

12. The method of claim 1 further comprising extracting the food product with a solvent thereby forming the sample.

13. The method of claim 12, wherein the solvent comprises an alcohol and optionally water.

14. The method of claim 12, wherein the solvent comprises at least one of methanol and ethanol and optionally water.

15. The method of claim 1, wherein the food product comprises a fruit, a tuber, a vegetable, a fungi, a nut, a legume, a cereal, a rhizome, a meat, an egg, a seafood, a traditional Chinese medicine, or a mixture thereof.

16. The method of claim 1, wherein the food product comprises a fruit, a tuber, a vegetable, a fungi, a nut, a legume, a cereal, a rhizome, or a mixture thereof.

17. The method of claim 4, wherein the food product comprises *Amomum kravanh* fruit, *Anemarrhena asphodeloides* rhizome, *Angelica dahurica* root, *Angelica sinensis* root, *Atractylodes macrocephala* rhizome, *Aletilla striata* tuber, *Codonopsis pilosula* root, *Dioscorea opposita* rhizome, apple, apricot, ginger, guava, peach, pear, pineapple, potato, strawberry, *Gastrodia elata* tuber, *Glehnia littoralis* root, *Glycyrrhiza uralensis* root, *Ligusticum chuanxiong* rhizome, *Lilium brownii* bulb, *Opphiopogon japonicus* root tuber, *Paeonia lactiflora* root, *Panax ginseng* root, *Platycodon grandiflorum* root, *Pueraria lobata* root, grape, papaya, starch, star fruit, mango, snow fungus, garlic, onion, cashew, *Citrus medica* fruit, *Crataegus pinnatifida* fruit, banana, blueberry, fig, kiwi, longan pulp, olives, *Lycium barbarum* fruit, macadamia nut, *Prunus armeniaca* seed, pistachios, *Pseudostellaria heterophylla* root, *Ziziphus jujuba* fruit, or a mixture thereof.

18. The method of claim 1, wherein the sulfur-treated food product was treated with sulfur-fumigation, sodium sulfate, sodium bisulfite, sodium metabisulfite, or a mixture thereof.

19. A method of identifying a sulfur-treated food product, the method comprising:

providing a sample comprising a food product;

analyzing the sample using an analytical method selected from the group consisting of high-performance liquid chromatography (HPLC-MS/MS) and ultra-performance liquid chromatography (UPLC-MS/MS) thereby generating mass spectroscopy data;

determining whether the mass spectroscopy data comprises one or more first markers indicative of the presence of tryptophan sulfonate, wherein the one or more first markers comprise an observed mass to charge ratio (m/z) selected from the group consisting of 283.04±0.01, 267.02±0.01, and 222.02±0.01; and identifying based on whether the mass spectroscopy data comprises the one or more first markers indicative of the presence of tryptophan sulfonate that the food product is sulfur-treated, wherein the presence of one or more first markers indicative of the presence of tryptophan sulfonate indicates that the food product is sulfur-treated.

20. The method of claim 19, wherein the food product comprises a fruit, a tuber, a vegetable, a fungi, a nut, a legume, a cereal, a rhizome, a meat, an egg, a seafood, or a mixture thereof.

* * * * *